(12) United States Patent
Tuschel

(10) Patent No.: US 7,580,126 B2
(45) Date of Patent: Aug. 25, 2009

(54) METHOD AND APPARATUS FOR PRODUCING A STREAMING RAMAN IMAGE OF NUCLEATION, AGGREGATION, AND CHEMICAL INTERACTION

(75) Inventor: David Tuschel, Monroeville, PA (US)

(73) Assignee: ChemImage Corp., Pittsburgh, PA (US)

( * ) Notice: Subject to any disclaimer, the term of this patent is extended or adjusted under 35 U.S.C. 154(b) by 166 days.

(21) Appl. No.: 11/268,590

(22) Filed: Nov. 8, 2005

(65) Prior Publication Data

US 2006/0126062 A1    Jun. 15, 2006

Related U.S. Application Data

(63) Continuation-in-part of application No. PCT/US2005/023638, filed on Jun. 30, 2005, and a continuation-in-part of application No. 10/882,082, filed on Jun. 30, 2004, now Pat. No. 7,046,359.

(60) Provisional application No. 60/720,432, filed on Sep. 26, 2005, provisional application No. 60/625,882, filed on Nov. 8, 2004.

(51) Int. Cl.
   *G01J 3/44* (2006.01)
(52) U.S. Cl. .................................................. 356/301
(58) Field of Classification Search ................ 356/301, 356/346, 436
   See application file for complete search history.

(56) References Cited

U.S. PATENT DOCUMENTS

| | | | |
|---|---|---|---|
| 5,377,003 A | 12/1994 | Lewis et al. | |
| 5,528,393 A | 6/1996 | Sharp et al. | |
| 5,626,134 A | 5/1997 | Zuckerman | |
| 5,784,162 A * | 7/1998 | Cabib et al. | ........ 356/456 |
| 5,866,430 A | 2/1999 | Grow | |
| 5,910,816 A | 6/1999 | Fontenot et al. | |
| 6,002,476 A | 12/1999 | Treado | |
| 6,052,187 A | 4/2000 | Krishnan et al. | |
| 6,069,690 A | 5/2000 | Xu et al. | |
| 6,175,750 B1 | 1/2001 | Cook et al. | |
| 6,181,414 B1 | 1/2001 | Raz et al. | |
| 6,274,871 B1 | 8/2001 | Dukor et al. | |
| 6,300,618 B1 | 10/2001 | Tanaami et al. | |
| 6,483,641 B1 | 11/2002 | MacAuley | |
| 6,485,413 B1 | 11/2002 | Boppart et al. | |

(Continued)

FOREIGN PATENT DOCUMENTS

WO    PCT/CA98/00092    8/1998

OTHER PUBLICATIONS

Treado, et al., "Indium Antimonide (inSb) Focal Plane Array (FPA) Detection for Near-Infrared Imaging Miscroscopy," Applied Spectroscopy 48 (1994) p. 607.

(Continued)

*Primary Examiner*—Gregory J Toatley, Jr.
*Assistant Examiner*—Abdullahi Nur
(74) *Attorney, Agent, or Firm*—Duane Morris LLP

(57) ABSTRACT

The present disclosure describes methods and apparatus to produce a streaming image of a sample during a time period when an attribute of the sample is changing. The streaming image can be viewed in such a manner so as to be able to follow a visible change in an attribute of the sample. The sample may be undergoing nucleation, aggregation, or chemical interaction. The present disclosure also describes methods and apparatus to determine a change in an attribute of a sample by detecting, analyzing, and comparing spectra of the sample taken at different times during the time period when the attribute of the sample is changing. The sample may be undergoing nucleation, aggregation, or chemical interaction.

100 Claims, 18 Drawing Sheets

U.S. PATENT DOCUMENTS

| | | | |
|---|---|---|---|
| 6,522,408 B1* | 2/2003 | Bruck et al. | 356/436 |
| 6,640,130 B1 | 10/2003 | Freeman et al. | |
| 6,640,132 B1 | 10/2003 | Freeman et al. | |
| 6,697,665 B1 | 2/2004 | Rava et al. | |
| 6,741,884 B1 | 5/2004 | Freeman et al. | |
| 6,810,279 B2 | 10/2004 | Mansfield et al. | |
| 6,867,858 B2 | 3/2005 | Owen et al. | |
| 6,934,060 B2* | 8/2005 | Psaltis | 359/15 |
| 6,937,885 B1 | 8/2005 | Lewis et al. | |
| 2001/0044129 A1 | 11/2001 | Ling et al. | |
| 2004/0127778 A1* | 7/2004 | Lambert et al. | 600/318 |
| 2004/0233431 A1 | 11/2004 | Ganz et al. | |

OTHER PUBLICATIONS

Morris, Hoyt, Miller and Treado, "Liquid Crystal Tunable Filter Raman Chemical Imaging," Applied Spectroscopy, No. 50, No. 6, Jun. 1996 pp. 805-811.

Patrick J. Treado, "Chemical Imaging Reveals More Than The Microscope," Laser Focus World, Oct. 1995 pp. 1-7.

Morris, "Ultrasensitive Raman and Fluorescence Imaging Using Liquid Crystal Tunable Filters," SPIE vol. 2385, (1995) pp. 81-87.

Treado, et al., "Infrared Raman Spectroscopic Imaging," (Marcell Decker, 1992) pp. 71-108.

Treado, et al., "High-Fidelity Raman Imaging Spectrometry: A Rapid Method Using An Acousto-Optic Tunable Filter," Applied Spectroscopy, vol. 46, No. 8 (1992) pp. 1211-1216.

Treado, et al., "Near-Infrared Acousto-Optic Filtered Spectroscopic Microscopy: A Solid-State Approach To Chemical Imaging," Applied Spectroscopy, vol. 46, No. 4 (1992) pp. 553-559.

Morris, et al., "Imaging Spectrometers for Fluorescence and Raman Microscopy: Acousto-Optic and Liquid Crystal Tunable Filter," Applied Spectroscopy, vol. 48, No. 7, (1994) pp. 857-860.

Turner, et al., "LCTF Raman Chemical Imaging in the Near-Infrared," SIPE vol. 3061 (1997) pp. 280-283.

Miller, et al., "Multispectral Imaging with a Liquid Crystal Tunable Filter," SPIE vol. 2345, (1995) pp. 354-365.

* cited by examiner

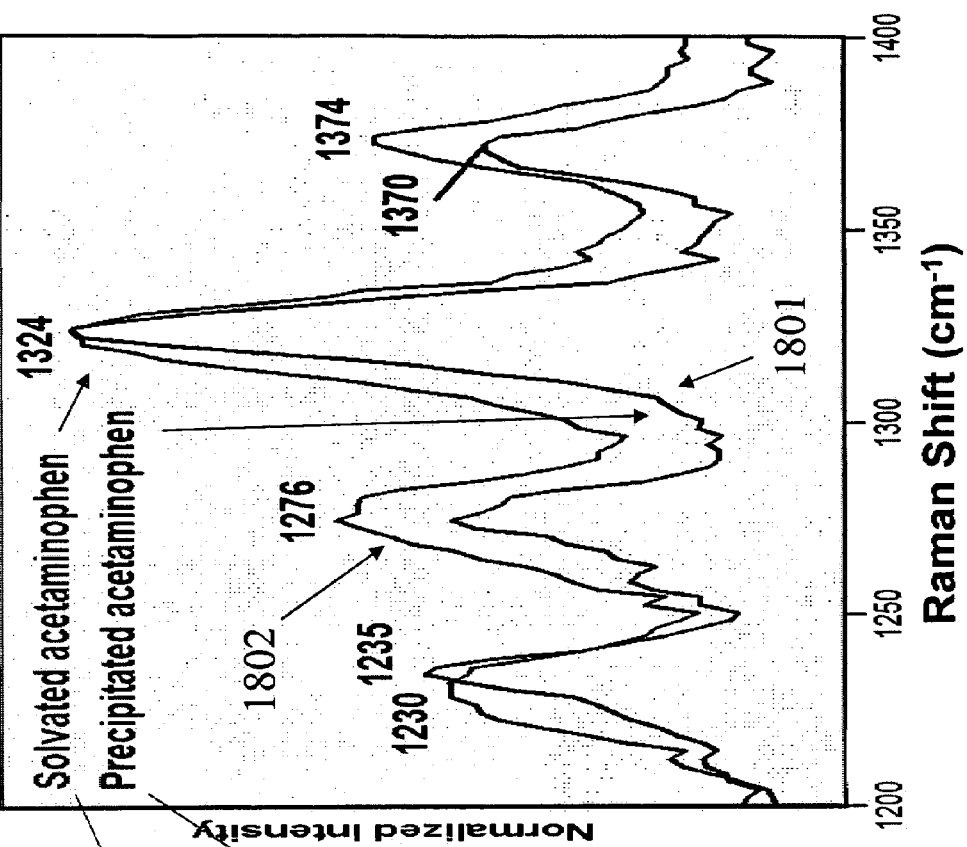
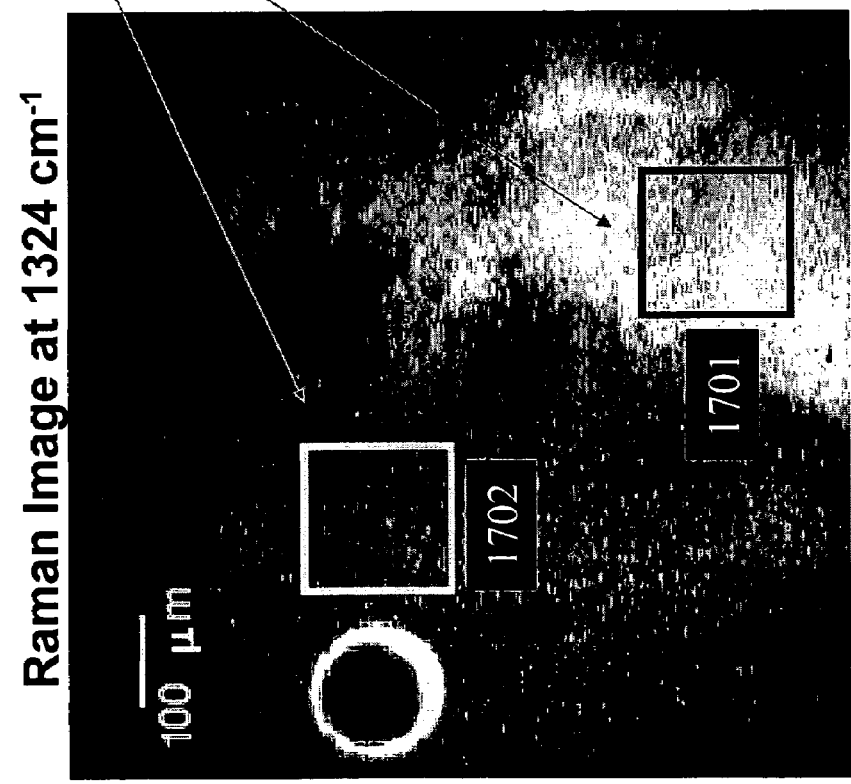
Figure 17
Figure 18

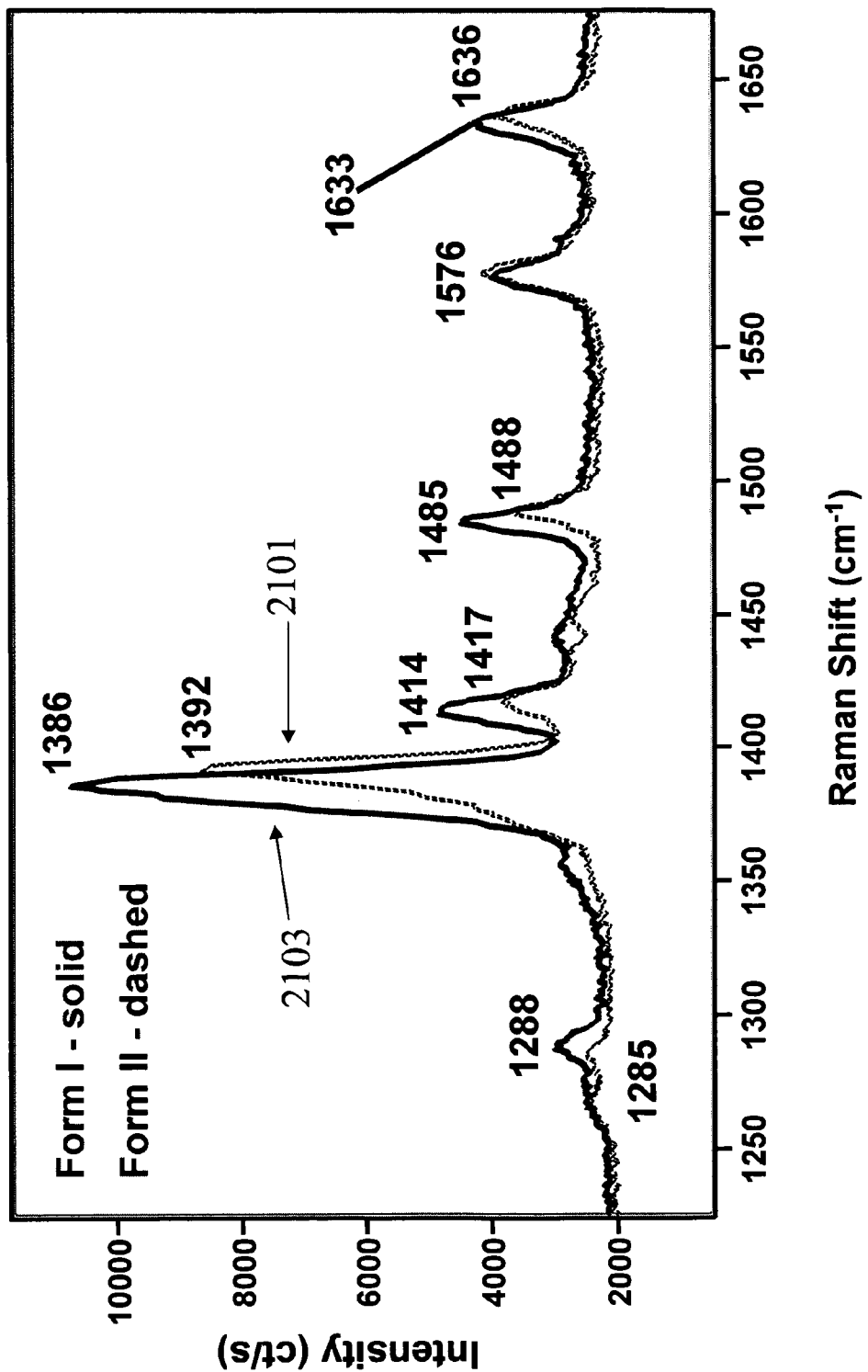

METHOD AND APPARATUS FOR PRODUCING A STREAMING RAMAN IMAGE OF NUCLEATION, AGGREGATION, AND CHEMICAL INTERACTION

PRIORITY CLAIMS AND CROSS-REFERENCES TO RELATED APPLICATIONS

The instant disclosure claims priority of U.S. Provisional Patent Application Ser. No. 60/720,432 filed 26 Sep. 2005 entitled "Raman Imaging of Nucleation, Molecular Aggregation and Chemical Interaction". The instant disclosure is a continuation-in-part of U.S. patent application Ser. No. 10/882,082 filed 30 Jun. 2004, now U.S. Pat. No. 7,046,359. The instant disclosure also is a continuation-in-part of Patent Cooperation Treaty Application No. PCT/US05/23638 filed 30 Jun. 2005 which claims priority to U.S. Provisional Patent Application Ser. No. 60/625,882 filed 8 Nov. 2004, each of which is incorporated herein by reference in its entirety. In addition, cross-reference is made to related U.S. application Ser. No. 11/268,591 filed concurrently herewith and entitled "Method and Apparatus for Determining Change in an Attribute of a Sample During Nucleation, Aggregation, or Chemical Interaction" which is also incorporated herein by reference in its entirety.

BACKGROUND

A complete theory describing the nucleation, aggregation, and subsequent crystallization of solvated molecules or ionic species does not currently exist, and a principal reason for this is the paucity of experimental evidence to support or refute theoretical hypotheses. Currently, a strong consensus in the art exists for a two step nucleation process. These steps are posited to comprise (1) the formation of clusters, solvated, but with some degree of chemical interaction and a degree of order beyond that found in the "normal" solvated state; and (2) the subsequent arrangement of the solvated species to a type of protocrystal. The latter step is believed to be the rate-determining step for crystallization.

One of the more promising methods of analysis currently being used to study crystal growth is atomic force microscopy. However, the information gained from the use of this technique is restricted to the understanding of epitaxial growth on existing crystal surfaces. Therefore, this method cannot be applied to the study of nucleation prior to the existence of a single unit cell.

With the successful demonstration of our dynamic chemical imaging in general, and dynamic Raman imaging in particular, new possibilities emerge for the molecular specific imaging of important time dependent phenomena in many varied fields, such as biology, organic chemistry, inorganic chemistry, biochemicals, and fabrication of semiconductor materials, to name a few. Raman scattering is extremely sensitive to crystal structure and even to orientation in soft materials. In particular, we can see the nucleation and aggregation that heretofore had been hidden.

Through the development of our dynamic chemical imaging capabilities, chemical insight into nucleation (prior to crystallization) and aggregation through spectral imaging of dynamic processes is now available to us for development through "Streaming Imaging" of crystal dissolution and subsequent recrystallization. This Streaming Imaging, or chemical imaging of dynamic processes, is now a reality and there is great potential to reveal many chemical and physical processes that have been "invisible" because of the absence of techniques for "seeing" transient processes.

Understanding and controlling crystallization is essential for the manufacture of products as varied as electronic devices, large-tonnage commodity materials, and high-value specialty chemicals such as pharmaceuticals. Yet understanding of the crystallization process remains limited, especially for organic, polymeric, and protein crystals. Once a crystal has formed, its internal structure can be determined by x-ray diffraction, but unraveling the key steps leading up to and during the process of crystallization requires tools that allow for control and microscopic visualization of crystal growth, particularly at the early stages that often determine crystal properties such as defect density, purity, size, morphology, and polymorphism (the ability of a material to adopt different crystal structures). The ability to view crystallization events directly, at the level of the individual growth unit, promises insights into the influence of experimental condition on crystallization at the near-molecular level, rather than by inference from characterization of bulk crystals.

In the area of biology, the occasional conversion of proteins from their intricately folded functional forms into thread-like molecular aggregates is not well understood. These transformations into an alternative form of protein structure are of much more than academic interest since such aggregates are linked to some of the most feared diseases of the modern era. These molecular aggregates are usually known as amyloids, or amyloid-like fibrils, and are perhaps most notorious for their association with Alzheimer's disease. However, amyloids are also involved in some twenty other protein "misfolding" disorders, including type II diabetes, the transmissible forms of the diseases epitomized by scrapie, "mad cow" disease in domesticated animals, and by kuru and Creutzfeldt-Jakob disease in humans. The proteins involved in these conditions are known as prions (proteinaceous infectious particles). Prions are increasingly turning up in different organisms, particularly yeast and other fungi. The yeast prions are not functionally or structurally related to their mammalian namesakes, and their ability to convert into fibrillar aggregates is coupled not just to disease but also to the inheritance of genetic traits. Proteins in amyloid fibrils are folded to produce a core region consisting of a continuous array of beta-sheets. Such sheets are a familiar type of protein motif, and here are made up of beta-strands that are oriented perpendicular to the fibril axis in an arrangement called a cross-beta structure. The ability to form this type of structure may be a generic feature of polypeptide chains, although the specific amino-acid sequence of the chain affects both the propensity to form fibrils and the way a given molecule is arranged within the fibrils. Knowledge of this latter aspect is vital for understanding the properties of protein forms such as prions, but has been seriously limited by the intractability of amyloid fibrils to the traditional methods of structural biology. Although much theoretical work has been published on the subject, there has never been much supporting experimental work because the right technological tools have not been available.

Additionally, embodiments of the disclosed method and apparatus may be used for visualizing, and therefore controlling, the existence of different crystalline forms of chemical compounds. Many chemical compounds can exist in multiple discrete crystalline forms. For example, graphite and diamond are discrete crystalline forms of elemental carbon. The property of being able to assume multiple crystalline forms is commonly designated polymorphism, and the different crystalline forms of the same compound are designated polymorphic forms or, more simply, polymorphs. Polymorphs of a single compound generally have chemical properties that vary in at least subtle ways. For instance, polymorphs can exhibit differences in melting points, electrical conductivities, patterns of radiation absorption, x-ray diffraction patterns, crystal shapes, dissolution rates, and solubilities, even though the polymorphs are made up of the same chemical.

In the context of pharmaceutically active compounds, differences among polymorphs can affect the pharmacological properties of the compound in significant ways. By way of example, the dissolution rate of a drug can greatly influence the rate and extent of bioavailability of the drug when administered by a selected route. Furthermore, the shelf stability of a drug compound can vary significantly, depending on the polymorphic form the drug assumes. In the U.S. and elsewhere, regulatory approval of a drug formulation often requires knowledge and description of the polymorphic form(s) of the drug that occur in the composition submitted for approval. This is so because approvability of a drug substance requires reproducibility in manufacture, dosing, and pharmacokinetic behavior of the drug. In the absence of such reproducibility, safety and efficacy of the drug cannot be sufficiently assured.

The polymorphic form(s) of a compound that are present in a composition is important in other industries as well. By way of example, the properties of dyes and of explosives can be strongly influenced by polymorphism. The crystalline form(s) present in a food product can affect the taste, mouth feel, and other properties of the product.

The crystal shape that a chemical compound assumes can be heavily influenced by the polymorphic form assumed by the compound. In turn, the bulk properties of a preparation of a compound in crystalline form(s) depend on the polymorphic form(s) assumed by the compound in the preparation. For instance, the flow characteristics, tensile strength, compressibility, and density of a powdered form of a compound will be determined by the polymorphs present in the preparation.

Various techniques are known for investigation of polymorphic forms of a compound that occur in the solid state. Such methods include polarized light microscopy (including hot-stage microscopy), infrared spectrophotometry, single-crystal X-ray and X-ray powder diffraction, thermal analysis, and dilatometry. In many instances, these methods can be limited by resolution of the method, polymorphic non-homogeneity of the analyte, similarity among polymorphs of the property analyzed, or other practical difficulties. In particular, compositions that contain multiple polymorphic forms of a compound can be difficult or impossible to analyze using such techniques.

Improved methods and apparatus for assessing the polymorphic forms of a compound, particularly in a solid particulate form and methods for influencing the polymorphic form assumed by a compound could overcome or limit the shortcomings identified above. Additionally, improved methods and apparatus are needed for visualizing the change of an attribute of a sample, such as, but not limited to, nucleation, aggregation, and subsequent crystallization of solvated molecules or ionic species, molecular specific imaging of time dependent phenomena, understanding and controlling crystallization, and conversion of proteins into prions. Obtaining a streaming image and/or comparison of spectra from a sample undergoing a change is necessary to realize the above goals.

Therefore, it is an object of the present disclosure to provide a method and apparatus for producing a streaming chemical image of photons scattered by, or emitted by, a sample where an attribute of the sample changes as a function of time.

It is another object of the present disclosure to provide a method and apparatus for determining a change in an attribute of a sample by detecting, analyzing, and comparing spectra of the sample where the attribute changes as a function of time.

BRIEF DESCRIPTION OF THE FIGURES

FIG. 17 is a Raman image at 1324 $cm^{-1}$ of a solid solution of acetaminophen in polyvinypyrrolidone showing solvated acetaminophen and precipitated acetaminophen.

FIG. 18 is a spectrum of solvated acetaminophen and a spectrum of precipitated acetaminophen.

FIG. 21 is a graph detailing the differences in the Raman spectra between an original crystallized form of nabumetone and a recrystallized form of nabumetone from FIG. 19.

DETAILED DESCRIPTION

The present disclosure describes methods and apparatus to produce a streaming image of a sample during a time period when an attribute of the sample is changing. The streaming image can be viewed in such a manner so as to be able to follow a visible change in an attribute of the sample. The present disclosure also describes methods and apparatus to determine a change in an attribute of a sample by detecting, analyzing, and comparing spectra of the sample taken at different times during the time period when the attribute of the sample is changing.

Figure 1:
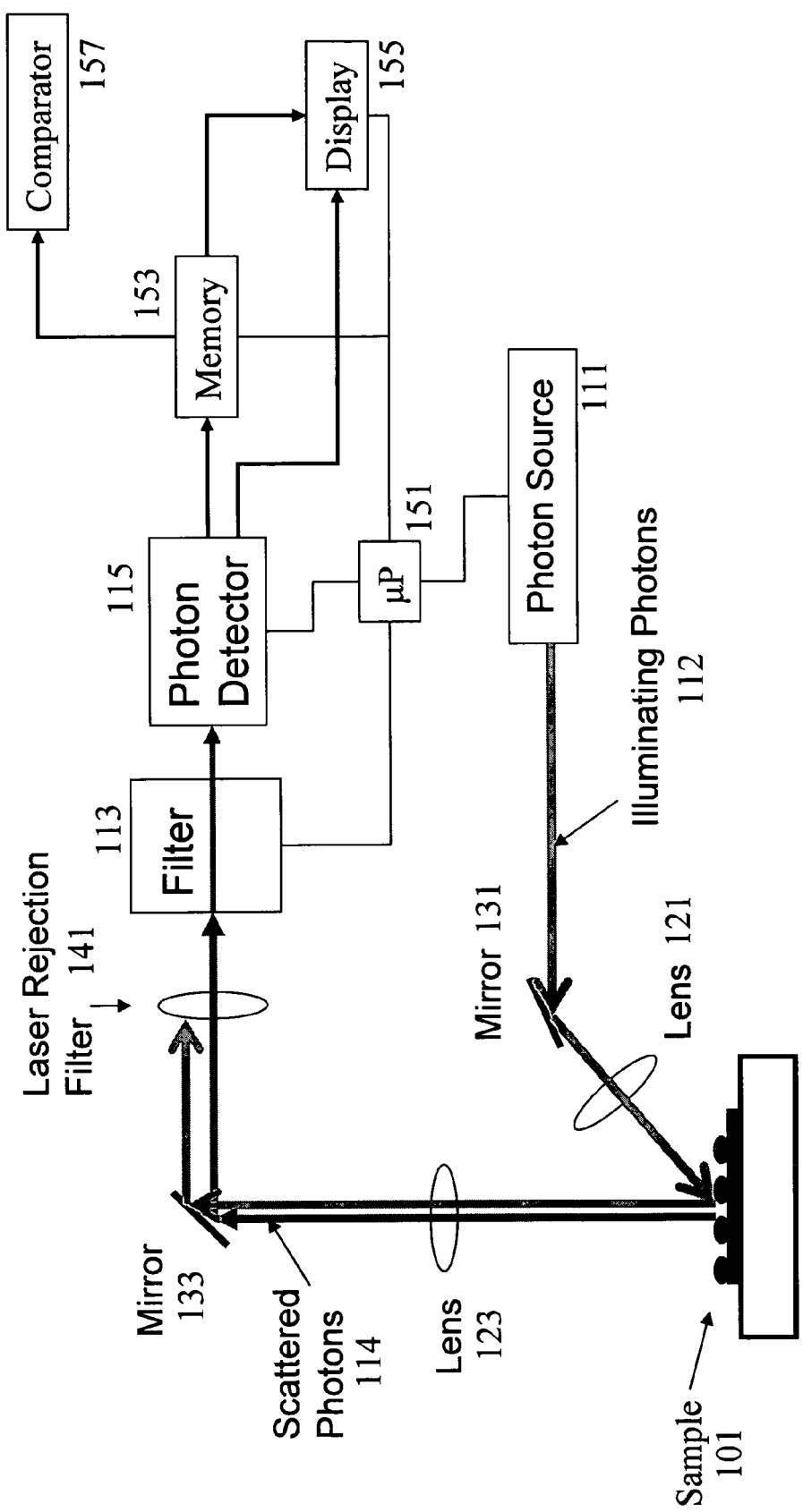
FIG. 1 is a schematic representation of an apparatus according to a disclosed embodiment.

Referring now to FIG. 1, the sample 101 from which the streaming image and/or the spectra are taken can be chosen from a wide variety of objects, chemicals, biological material, elements, compounds, crystals, or manufactured products such as, but not limited to, acetaminophen, semiconductor material, protein, amyloid, prion, covalent crystal, ionic crystal, metallic crystal, and molecular crystal.

An attribute of the sample 101 may be one, or a combination, of any number of characteristics, qualities, or features such as, but not limited to, spatial displacement, chemical interaction, chemical state, physical state, phase, growth, shrinkage, diffusion, chemical decomposition, chemical metabolization, and physical strain. Additionally, an attribute of the sample may be crystallization, dissolution, nucleation, or aggregation. Furthermore, an attribute of the sample may be defect density, purity, size, or morphology. The foregoing examples are not intended to be limiting and one of skill in the art can readily ascertain that other attributes are contemplated by the disclosed methods and apparatus.

As is obvious to those of skill in the art, the time period over which the above-mentioned attributes change varies from attribute to attribute and compound to compound. Therefore, the time period between obtaining a first wavelength(s) specific image, spectral image, or spectra and obtaining a second image or spectra will vary based on a variety of factors. One of those factors may be a function of the amount of time to detect a visual change in the sample 101 due to a change in one of the attributes. For example, if an attribute changes at a rate such that a visible change in the sample 101 from one image to the next takes a particular amount of time, it may be advantageous to adjust the time period between obtaining images of the sample 101 so that the time period of obtaining the images is on the order of, or approximately equal to, the particular amount of time to see a visible change in the sample. Time periods ("$\Delta t$") between obtaining images may be selectable and need not be the same between differing pairs of images or spectra. Time periods $\Delta t$ that have been determined to be of interest include, but are not limited to, the following intervals: $\Delta t$ is approximately one second; 0 sec.$<\Delta t \leq 1$ sec.; 1 sec.$\leq \Delta t \leq 30$ sec.; 1 min.$\leq \Delta t \leq 5$ min.; and 0 min.$<\Delta t \leq 10$ min. Those of skill in the art will readily understand that other time periods are also contemplated by the present disclosure.

A technology that may be advantageous, but not a requirement, for producing an image of a sample 101 is referred to herein as "dark field" imaging. In dark field imaging, the sample is illuminated with photons that do not pass through the optical train of the image capture optics. The illuminating photons may form an oblique (i.e., non-parallel) angle to the sample normal (measured either above or below the plane of the sample) as shown in FIG. 1 or the illuminating photons may illuminate the sample from a side that is opposite the side from which the optical train is disposed. The dark field technique may be used advantageously for imaging nucleation and aggregation.

Referring again to FIG. 1 which depicts an apparatus according to one embodiment of the disclosure, the photon source 111 provides the illuminating photons 112 which illuminate the sample 101 via a mirror 131 and a lens 121. The sample 101 has an attribute, as discussed above, which undergoes a change. As would be obvious to those of skill in the art, the mirror 131 and the lens 121 may each individually not be required depending on, among other things, the configuration of the apparatus. The illuminating photons 112 interact with the sample 101 to produce the scattered photons 114 which are directed towards the filter 113 via the lens 123, the mirror 133 and the laser rejection filter 141. As would be obvious to those of skill in the art, the lens 123, the mirror 133, and the laser rejection filter 141 may each individually not be required to provide the scattered photons 114 to the filter 113. The filter 113 is advantageously a tunable filter which allows photons of a specific wavelength or photons with a wavelength within a range of wavelengths to pass through. The scattered photons that pass through the filter are then detected by the photon detector 115.

The output of the photon detector 115 may be used to form a spatially accurate wavelength-resolved image. A spatially accurate wavelength-resolved image may be an image of the sample 101 that is formed from multiple "frames" wherein each frame has plural spatial dimensions and is created from photons of a particular wavelength (or wave number) or from photons in a particular wavelength band (or wave number band) so that the frames may be combined to form a complete image across all wavelengths (wave numbers) of interest.

The photon detector 115 detects the photons that pass through the filter 113. The photon detector 115 may be controlled manually by an operator or automatically by, for example, the microprocessor device 151 ("µP") so as to obtain a first image (or first spectrum) of the sample 101 at a first time $t_1$ and a second image (or second spectrum) of the sample at a second time $t_2$ where $t_2$ occurs after $t_1$ by a predetermined amount of time $\Delta t$. Of course, if more than two images (or spectral images or spectra) of the sample 101 are desired, the microprocessor device 151 can control the photon detector 115 to take a third, fourth, fifth, etc., image (or spectra) at a specific time interval. The time interval between a first pair of images (or spectra) need not be the same as the time interval between a second pair of images (or spectra).

The output of the photon detector 115 may be an electronic signal representative of an image of the sample 101. In one embodiment, the image of the sample is a spatially accurate wavelength-resolved image of the sample. In another embodiment, the image of the sample is a spectrum. The output of the photon detector may be sent to the conventional electronic data memory device 153 for storage. Alternatively, the output of the photon detector may be sent directly to the display device 155 for displaying the image of the sample 101 in a visually-readable form. In one embodiment, a streaming image of the sample 101 may be produced by sequentially displaying images of the sample (akin to a movie being a sequential display of a number of still images) either from the memory 153 or directly from the photon detector 115.

In yet another embodiment, the memory device 153 may store a first and a second data stream output from the photon detector 115. The first and second data streams may then be output from the memory device to the comparator 157 where the first and second data streams may be combined and/or compared.

The photon source 111 is positioned to provide illuminating photons 112 to the sample 101. The photon source 111 can include any conventional photon source, including a laser, a light emitting diode, a white light source, and other infrared ("IR") or near IR devices. The photon source may be used in conjunction with a grating or a wavelength tunable filter, as is known in the art. In an embodiment of the disclosure, the wavelength of the photons supplied by the photon source is in the range of about 200 nanometers ("nm") to about 1100 nm. Alternatively, the illuminating photons may be substantially monochromatic. The photon source may provide polarized illuminating photons. The illuminating photons 112 may be deflected by the mirror 131 through the lens 121 which may optionally be used to focus the illuminating photons on the sample 101. Alternatively, the illuminating photons 112 may be directed towards the sample 101 without the need for the mirror 131. The microprocessor 151 may control the photon source 111.

The illuminating photons 112 may be scattered by the sample 101 to produce the scattered photons 114. The scattered photons may be Raman scattered photons. The scattered photons 114 are directed to the filter 113. The photons may be focused by the lens 123. The laser rejection filter 141 may be positioned prior to the filter 113 to filter out illuminating photons 112 to optimize the performance of the system. The filter 113 is advantageously a tunable filter, such as a conventional tunable filter including a liquid crystal tunable filter ("LCTF"), an acousto-optical tunable filter ("AOTF"), or any other electro-optical tunable filter. Alternatively, the filter 113 may be an imaging interferometer, as is known in the art. As stated above, a tunable filter allows photons of a specific wavelength or within a specific range of wavelengths to pass through while photons of other wavelengths are blocked. The specific wavelength or range of wavelengths that pass through the filter 113 can be chosen either by an operator or automatically by, for example, the microprocessor device 151. The wavelengths that can be passed through the filter 113 may range from 200 nm (ultraviolet) to 2000 nm (i.e., the near infrared). In an embodiment of the disclosure, the wavelength range of the filter 113 may be 200 nm to 1100 nm. The choice of wavelength depends upon a number of factors, such as, but not limited to, the desired optical region for the image or spectrum to be produced and/or the nature of the sample being analyzed. The microprocessor device may control the filter 113 and the photon detector 115 in unison or separately.

The photon detector 115 may be a charge coupled device ("CCD"), a complementary metal oxide semiconductor ("CMOS") camera, an avalanche photodiode array, a focal plane array, or other known photon detectors suitable for herein described embodiments. Additionally, there may be more than one detector used. For example, a first photon detector may be used to detect a first group of photons passing through a first filter and a second photon detector may be used to detect a second group of photons passing through a second filter.

The microprocessor 151 may be used to control each of the following components either individually, in groups, or all together: the photon source 111, the mirror 131, the lens 121, the lens 123, the mirror 133, the laser rejection filter 141, the filter 113, the photon detector 115, the memory device 153, the comparator 157, and the display 155. For clarity reasons, not all the connections from the microprocessor 151 to the components are shown.

Figure 2:
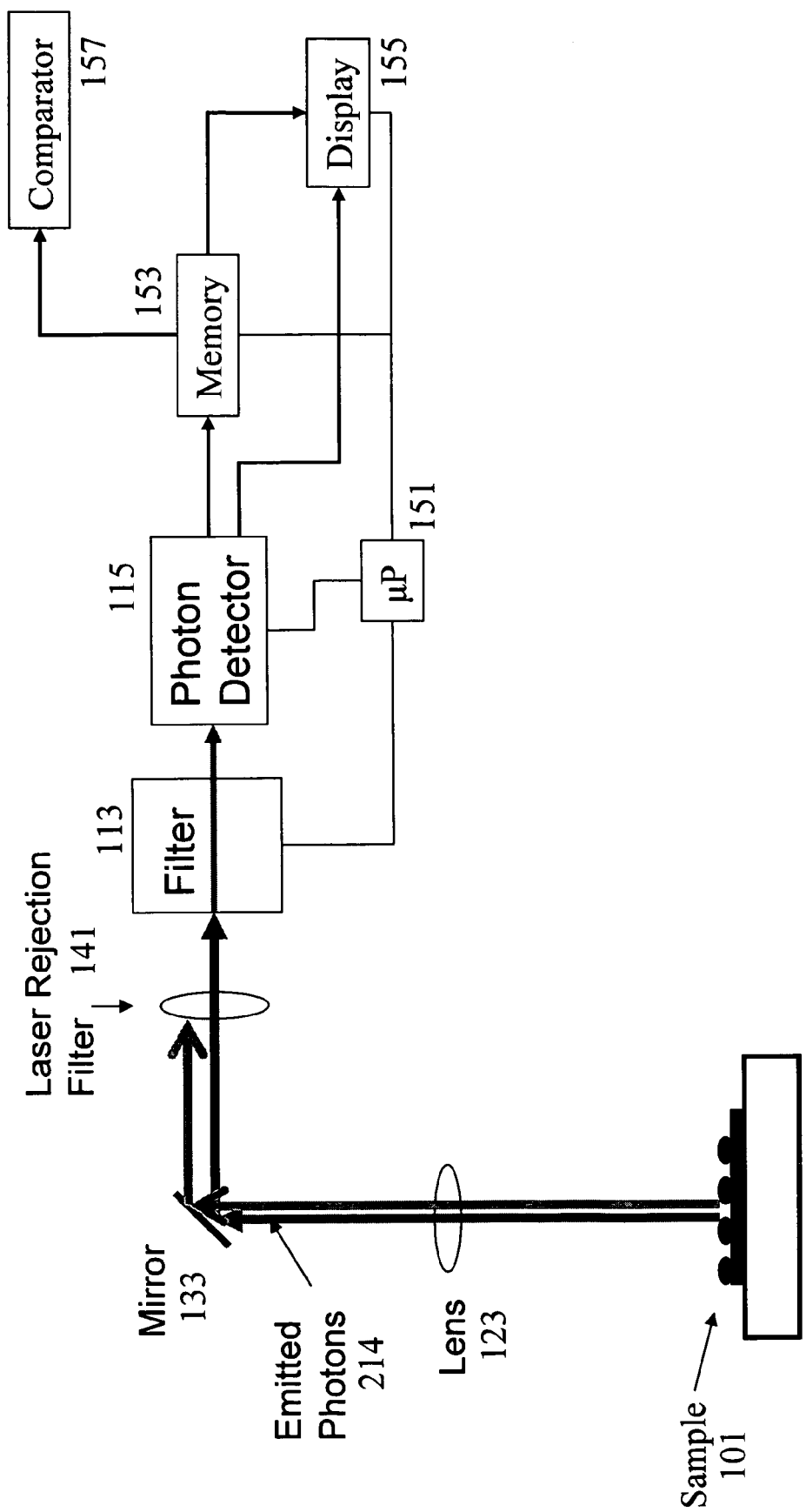
FIG. 2 is a schematic representation of an apparatus according to another disclosed embodiment.

With attention now drawn to FIG. 2, another embodiment of the disclosure is shown in which are photons emitted by the sample 101. Like numbers refer to like components in FIGS. 1 and 2. The embodiment depicted in FIG. 2 is similar to the embodiment depicted in FIG. 1 with the exception that in FIG. 2 there is no photon source and associated mirror and lens since for producing and directing illuminating photons to the sample 101. The emitted photons 214 from the sample 101 are directed towards the filter 113 and toward the photon detector 115 in a manner similar to the description above for the scattered photons 114 in FIG. 1. The emitted photons 214 may include, for example, photons produced by the sample through fluorescence, phosphorescence, photoluminescence, electroluminescence, chemiluminescence, sonoluminescence, thermoluminescence, and upconversion. When the emitted photons 214 reach the photon detector 115 (i.e., those that pass through the filter 113), the photon detector 115, the microprocessor 151, the memory 153, the display 155 and the comparator 157 operate in a manner similar to that described above with the scattered photons 114 to produce a streaming image of the sample 101 and/or comparing two or more images or spectra of the sample 101.

Figure 3:
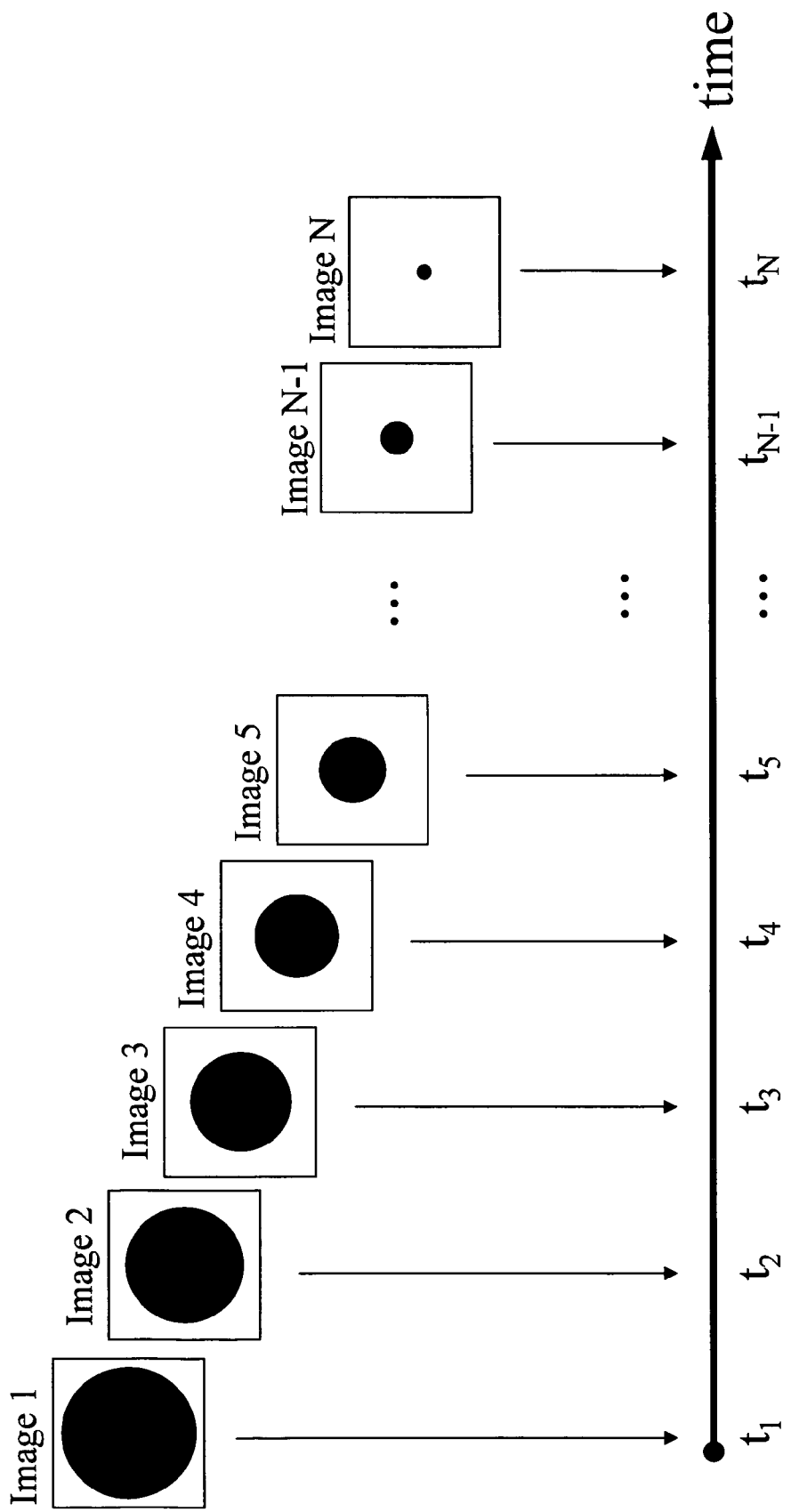
FIG. 3 is an illustration of a number of images, taken at different times, of a sample that is undergoing a change in an attribute.

FIG. 3 is an illustration of a number of images, taken at different times, of a sample that is undergoing a change in an attribute. In this depiction, the attribute that is changing is the size of the sample. Those of skill in the art will immediately understand that FIG. 3 is exemplary only and in no way limits the disclosed apparatus or methods. The images may represent spatially accurate wavelength-resolved images. In FIG. 3, an image is taken at each time interval: Image 1 is taken at time $t_1$, Image 2 is taken at time $t_2$, . . . , and Image N is taken at time $t_N$. It is not necessary that the time intervals be the same or that an image be taken at each time interval. The images may be stored in a memory device, such as the memory device 153 in FIGS. 1 and 2, and then displayed sequentially in the display device 155 to form a streaming image of the sample undergoing a change in an attribute. The images may also be displayed in real time by a display device, such as the display device 155 in FIGS. 1 and 2. The images may also be compared in a comparing device such as the comparator 157 in FIGS. 1 and 2.

FIGS. 4 through 11 are flow charts each showing the major steps in a particular method according to an embodiment of the disclosure. Reference numbers incorporating the same digit in the units column refer to similar steps for FIGS. 4 through 11. For example, the steps 501, 601, 701, 801, 901, 1001, and 1101 all refer to the step of providing a sample with a changing attribute. Reference numbers with the digit "3" in the units column refer to a filtering step. Reference numbers with the digit "5" or "7" in the units column refer to a first photon detecting step or a second photon detecting step, respectively. Reference numbers with the digit "9" in the units column refer to a displaying or comparing step.

Figure 4:
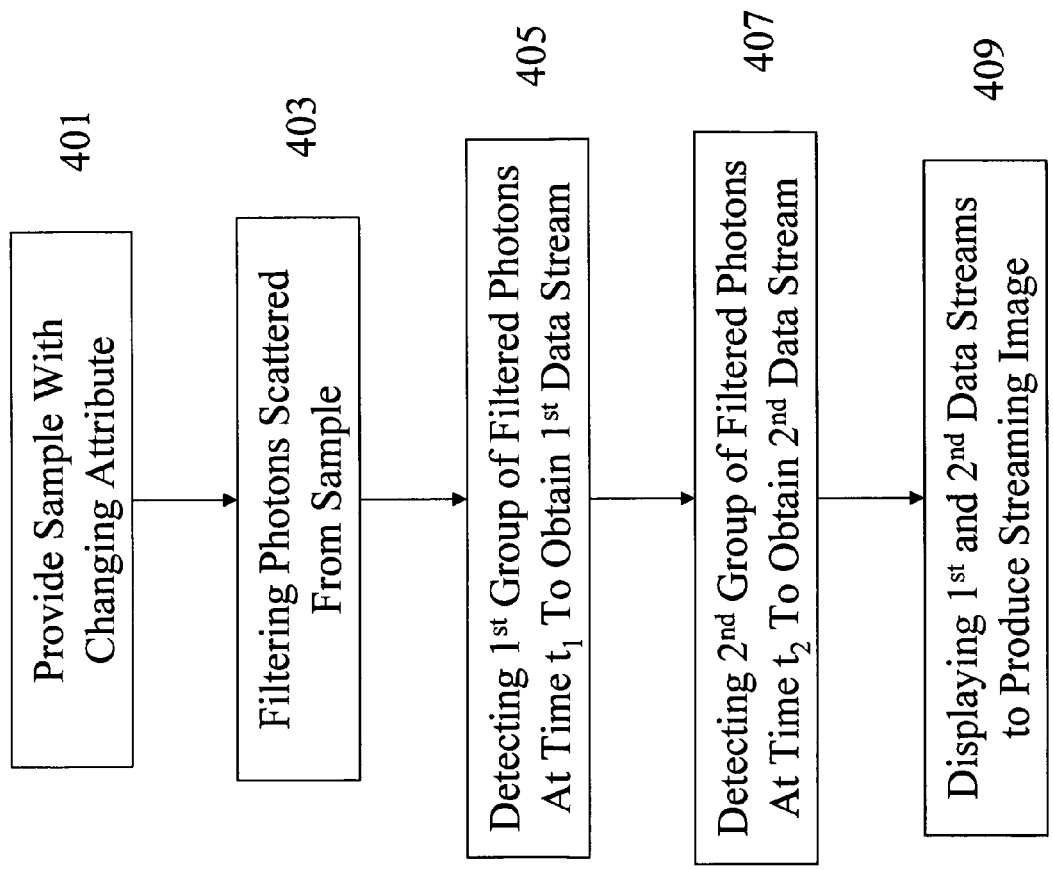
FIGS. 4 through 11 are flow charts each showing a set of major steps in a particular method according to an embodiment of the disclosure.

FIG. 4 refers to an embodiment for producing a streaming image of a sample with a changing attribute where the individual images are produced from photons scattered from the sample.

Figure 5:
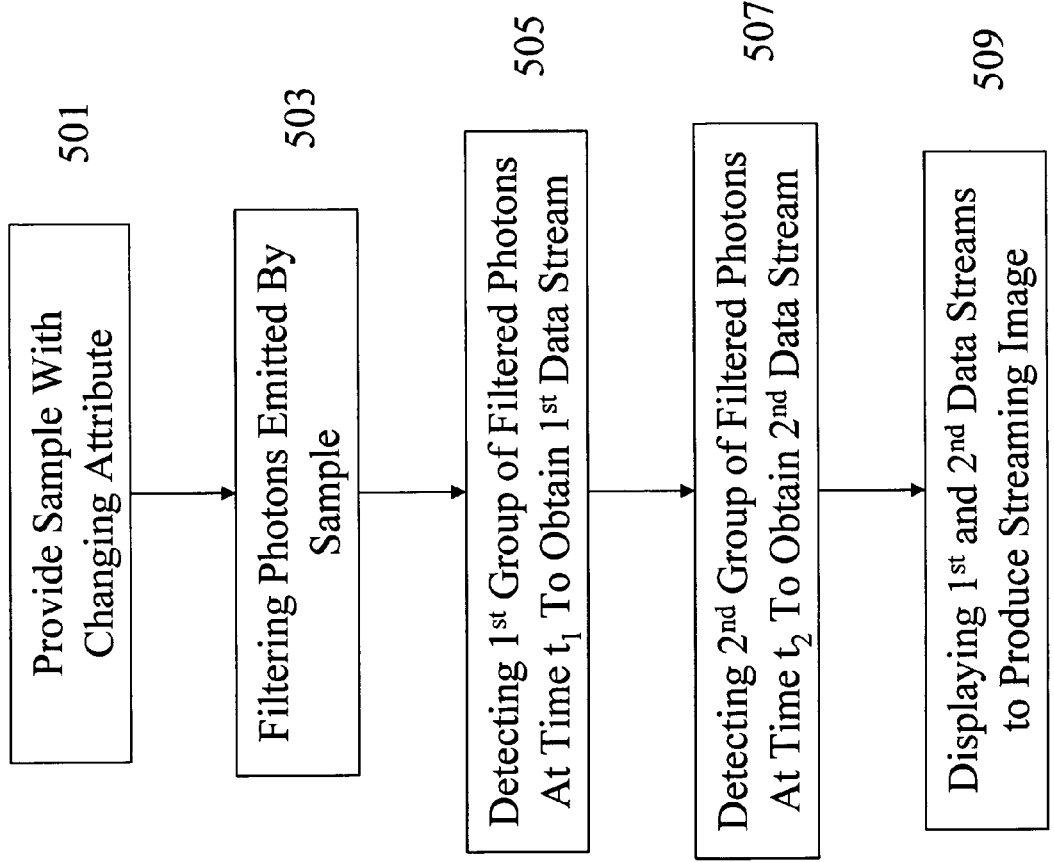

FIG. 5 refers to an embodiment for producing a streaming image of a sample with a changing attribute where the individual images are produced from photons emitted by the sample.

Figure 6:
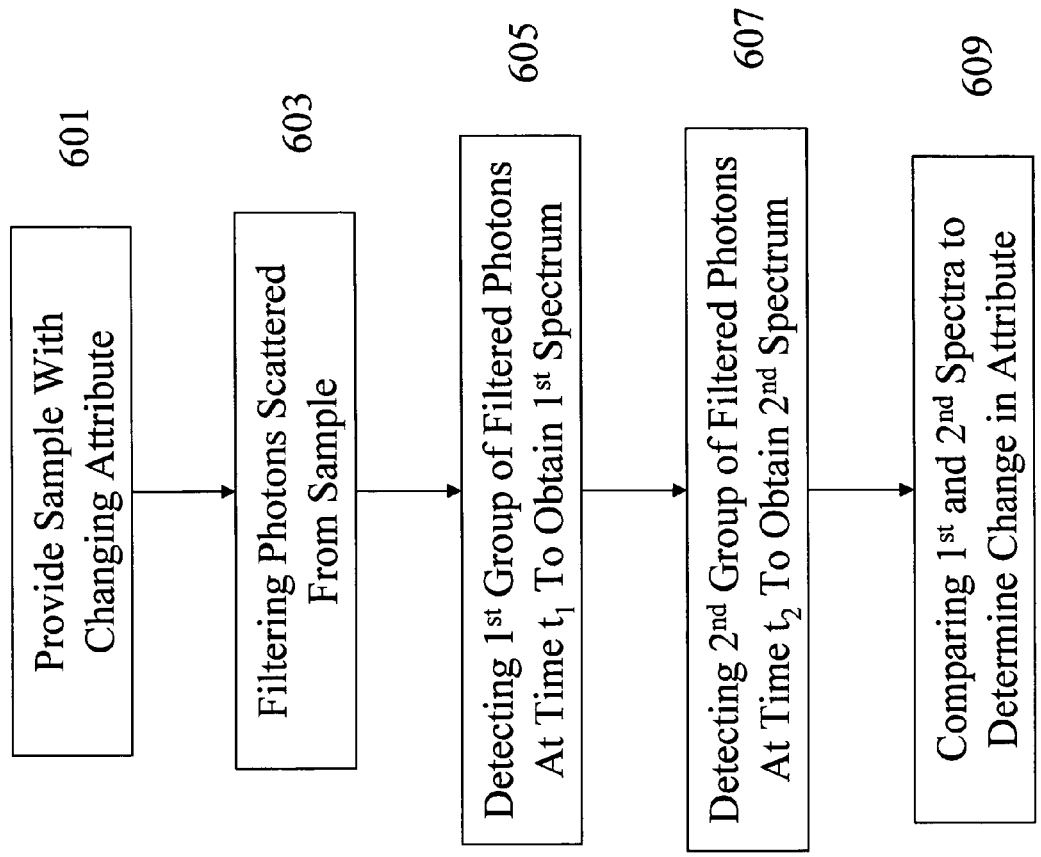

FIG. 6 refers to an embodiment for determining a change in an attribute of a sample where the spectra are produced from photons scattered from the sample.

Figure 7:
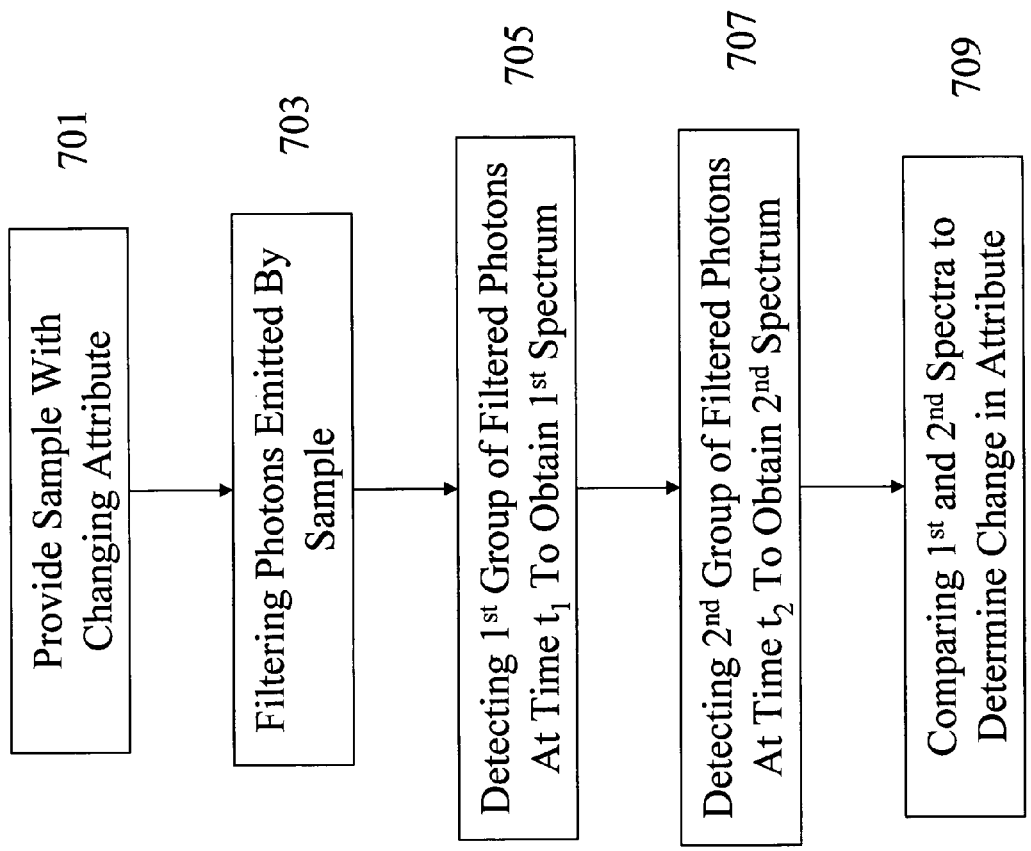

FIG. 7 refers to an embodiment for determining a change in an attribute of a sample where the spectra are produced from photons emitted by the sample.

Figure 8:
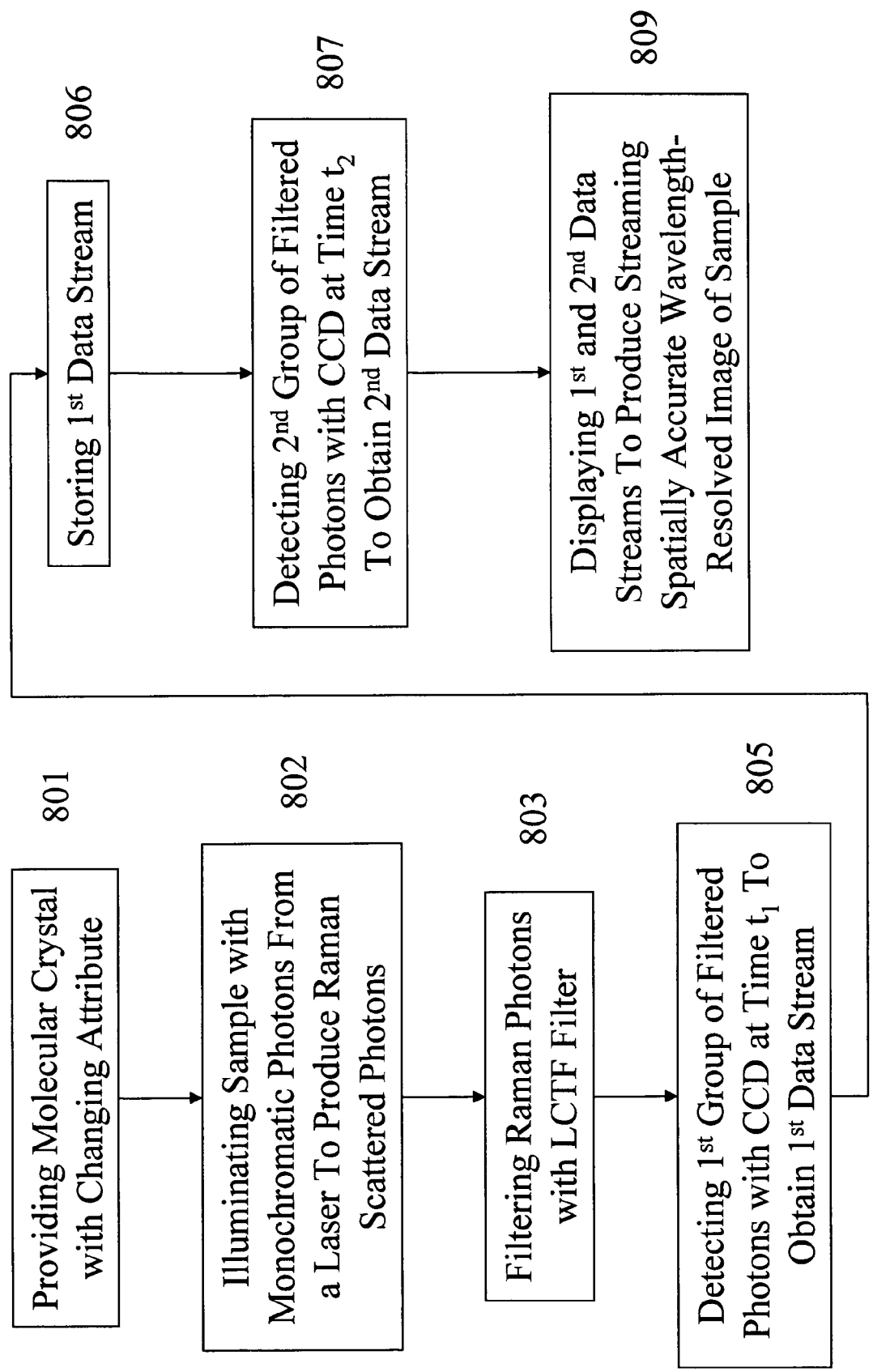

FIG. 8 refers to an embodiment for producing a streaming spatially accurate wavelength-resolved image of a material sample as it achieves a crystalline form with a changing attribute where the individual images are produced from Raman scattered photons from the sample.

Figure 9:
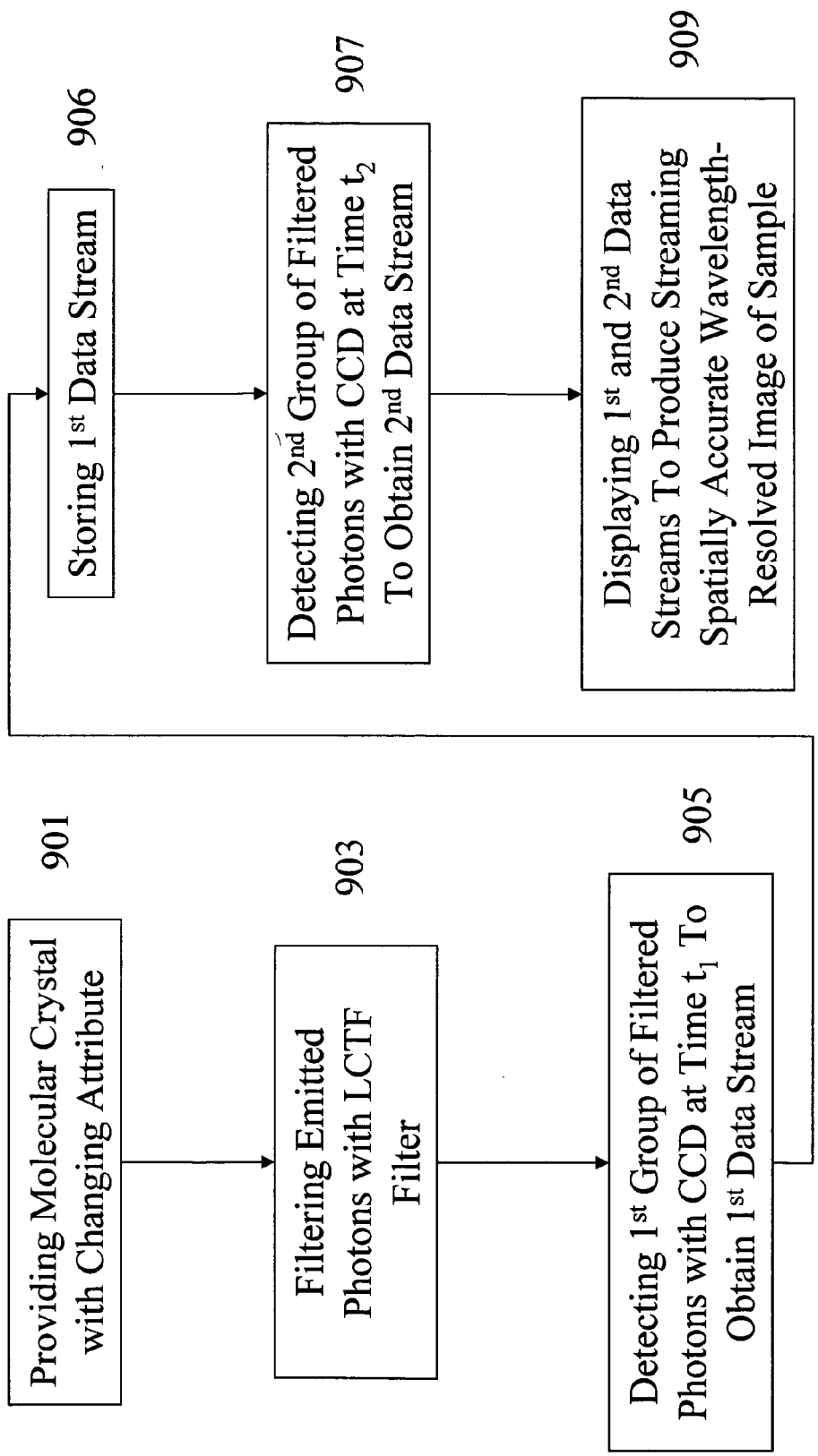

FIG. 9 refers to an embodiment for producing a streaming spatially accurate wavelength-resolved image of a material sample as it achieves a crystalline form with a changing attribute where the individual images are produced from photons emitted by the sample.

Figure 10:
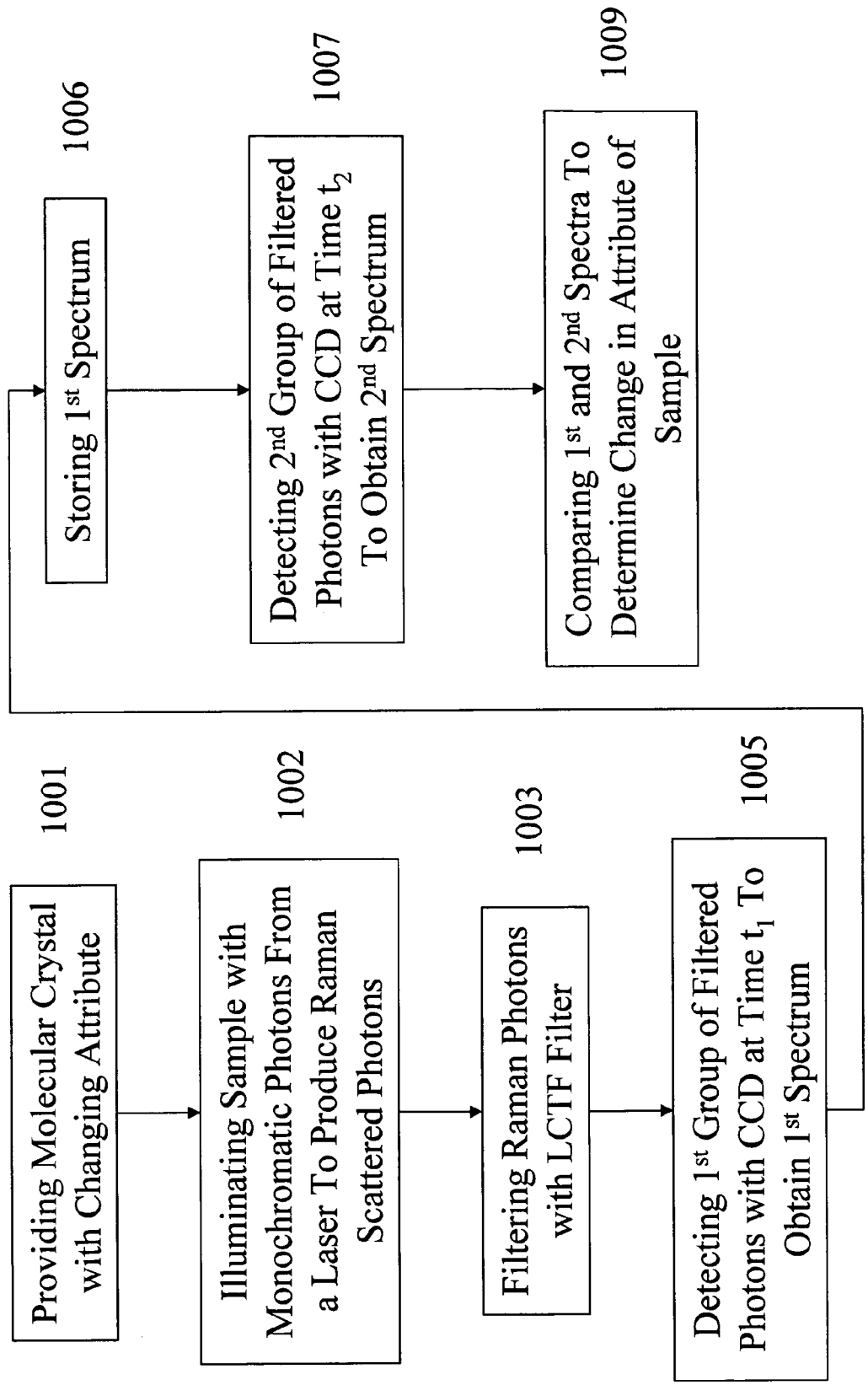

FIG. 10 refers to an embodiment for determining a change in an attribute of a material sample as it achieves a crystalline form where the individual spectra are produced from Raman scattered photons from the sample.

Figure 11:
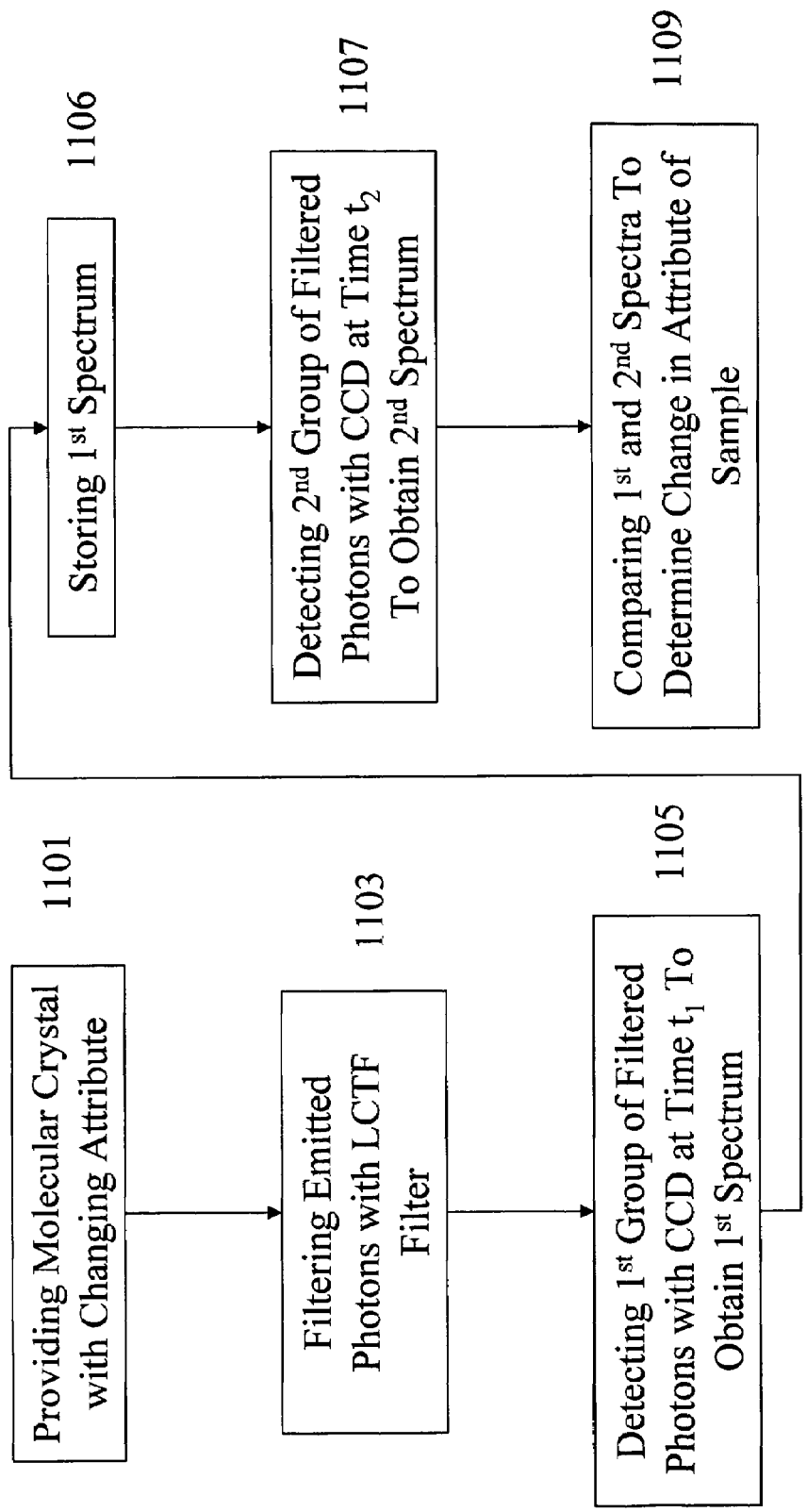

FIG. 11 refers to an embodiment for determining a change in an attribute of a material sample as it achieves a crystalline form where the individual spectra are produced from photons emitted by the sample.

Now turning attention to the output of the above apparatus and methods described above for various embodiments of the disclosure, the inventor has demonstrated the ability to obtain streaming Raman images of a sample that exhibits a time dependent phenomena or attribute. Specifically, streaming Raman images, or "movies", of the dissolution and subsequent recrystallization of aspirin in methanol have been produced. One of the Raman movies was produced at a wavenumber of 1607 $cm^{-1}$ and shows the dissolution of aspirin after a drop of methanol is placed on it from a pipette. The individual Raman images that were streamed together to create the movie were acquired at a rate of 1 sec/frame integration time over a duration of 50 seconds. This is by no means the only wavenumber, integration time, or duration for which a Raman movie may be obtained. Additionally, the method and apparatus used to produce the movie is not limited to Raman images but can be achieved by using other types of photons scattered by a sample or emitted by a sample. By the appropriate selection of a wavenumber or band of wavenumbers corresponding to a particular subject molecular species or other sample, one could image the generation and subsequent diffusion of the solvated molecules.

In addition to chemical imaging of dissolution, the inventor has demonstrated the ability to produce a Raman movie from streaming Raman images of the subsequent recrystallization upon volatilization (evaporation) of the solvent. As with the movie mentioned above showing the dissolution of aspirin after a drop of methanol is placed on it from a pipette, the method and apparatus used to produce the movie or recrystallization is not limited to Raman images but can be achieved by using other types of photons scattered by a sample or emitted by a sample. Additionally, a variety of wavenumber, integration time, and duration choices for the movie are available, as would be understood by those of skill in the art.

Furthermore, the inventor has used apparatus and methods according to embodiments of the disclosure to determine changes in other attributes of a sample. For example, differentiating crystalline from solvated, nucleating, or aggregating species through Raman imaging is made clear by the spectra shown in FIG. 12. The spectrum 1201 is the Raman spectrum of solid acetaminophen produced with a dark field Raman imaging apparatus according to an embodiment of the disclosure. The spectrum 1202 is the Raman spectrum of solvated acetaminophen produced with a dark field Raman imaging apparatus according to an embodiment of the disclosure. The spectra are of the same compound (acetaminophen) but they manifest significant differences sufficient to differentiate the states, solid or solvated, of the species. These differences are obvious from comparing, for example, the peaks of the spectra 1201 and 1202 as well as comparing the relative height of the peaks of the spectra (such differences are clearly demonstrated by the high resolution solvated and solid state acetaminophen spectra in FIG. 19. Thus, by collecting images at a wavenumber or band of wavenumbers corresponding to the molecular species, one could image the generation and diffusion of solvated molecules upon dissolution and the nucleation of them prior to crystallization.

Figure 12:
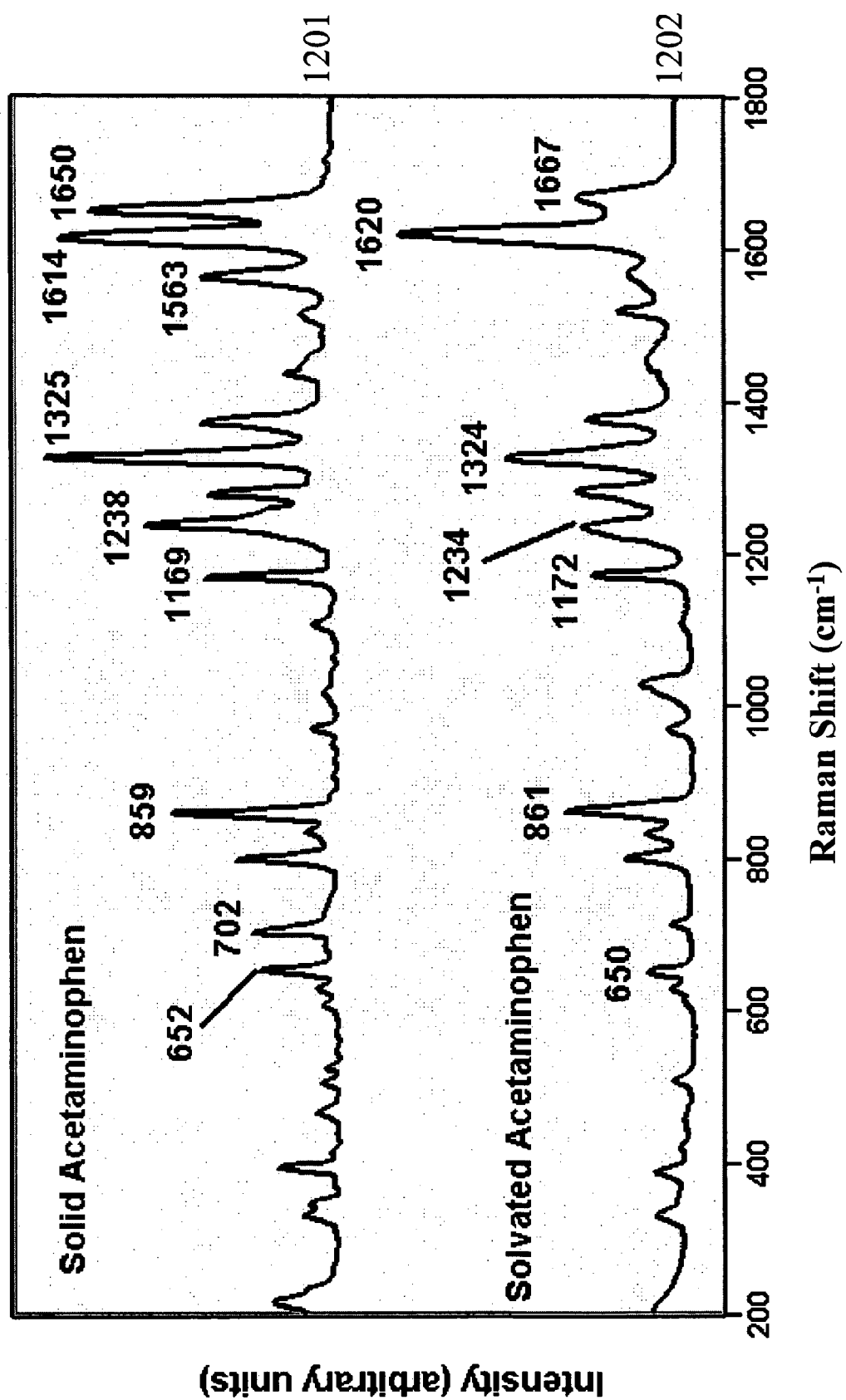
FIG. 12 is a graph showing the differences in the Raman spectra of solid acetaminophen and solvated acetaminophen produced with a dark field Raman imaging apparatus according to an embodiment of the disclosure.
Figure 13:
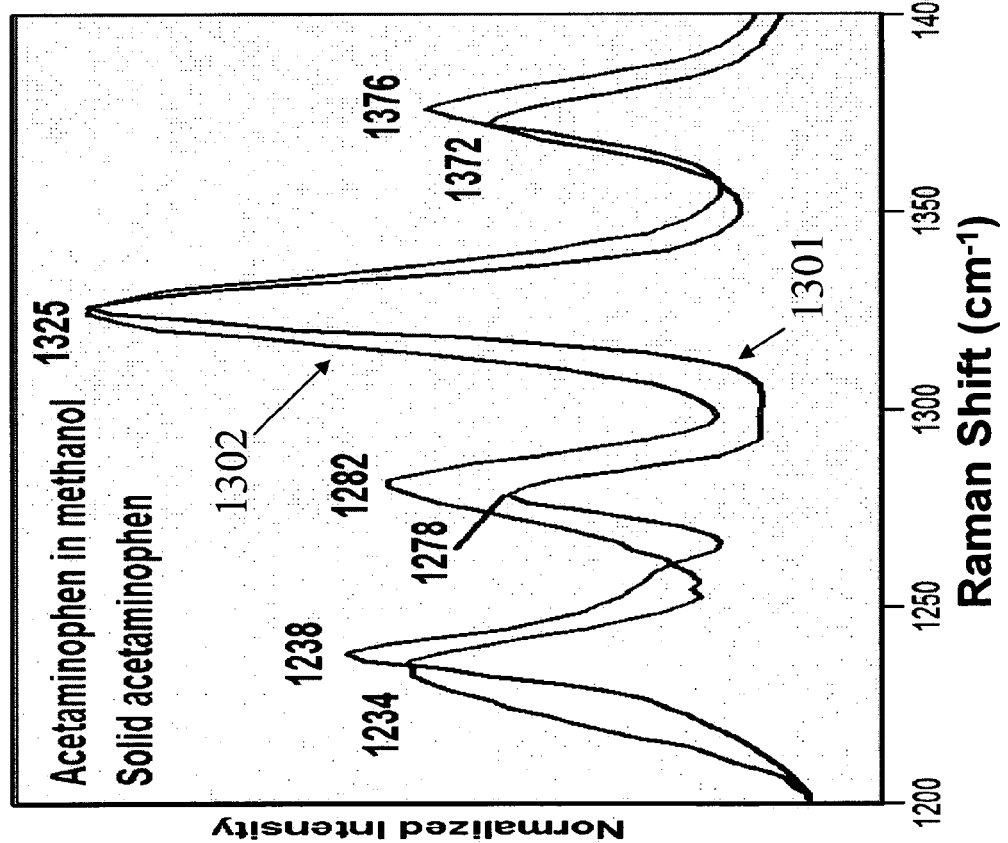
FIG. 13 is a graph detailing the differences in the Raman spectra of solid acetaminophen and solvated acetaminophen over a portion of the graph of spectra in FIG. 12.

FIG. 13 is a graph detailing the differences in the Raman spectra of solvated (in methanol) and solid acetaminophen over a portion of the Raman shift (x-axis) of FIG. 12 (i.e., 1200-1400 cm$^{-1}$). The spectrum 1301 is a Raman spectrum of solid acetaminophen. The spectrum 1302 is a Raman spectrum of acetaminophen solvated by methanol.

Figure 14:
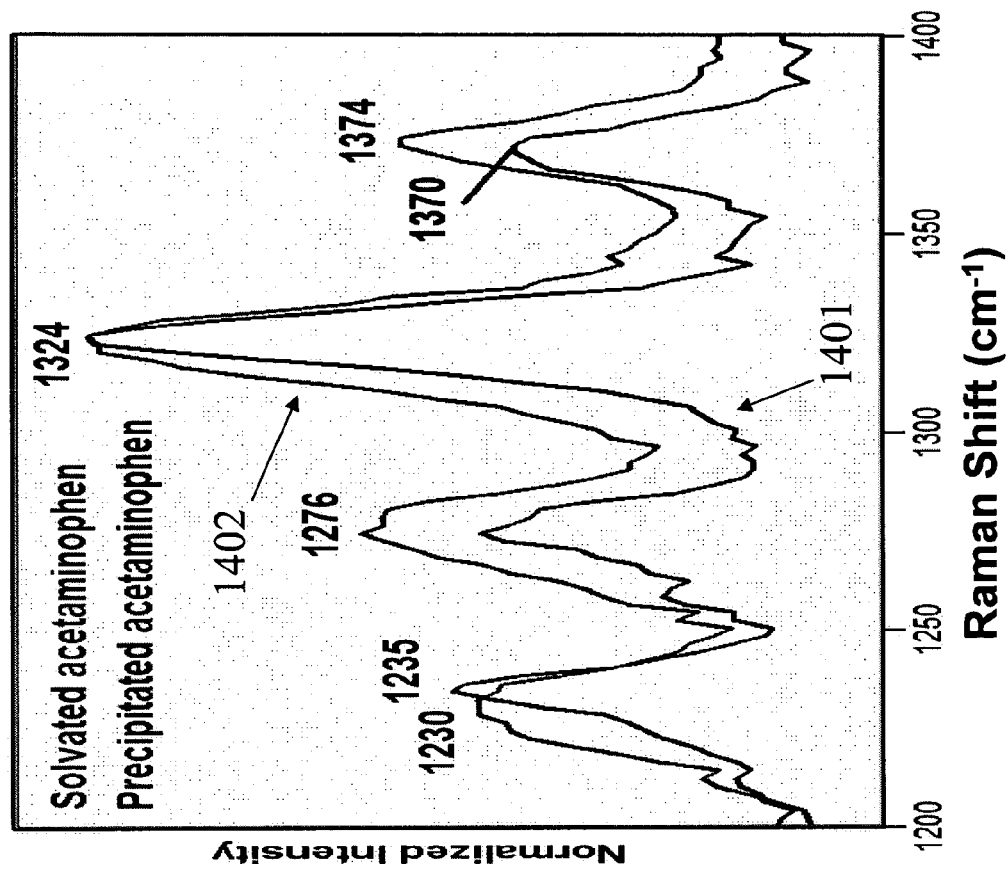
FIG. 14 is a graph detailing the differences in the Raman spectra of solvated acetaminophen and precipitated acetaminophen over a portion of the graph of spectra in FIG. 12.

FIG. 14 is a graph detailing the differences in the Raman spectra of solvated acetaminophen and precipitated acetaminophen over a portion of the graph of spectra in FIG. 12 (which is the same as for FIG. 13, i.e., 1200-1400 cm$^{-1}$). The spectrum 1402 is a Raman spectrum of acetaminophen solvated by a polyvinypyrrolidone, a polymer, and is extracted from the Raman image shown in FIG. 15 (spectrum 1402 is also the same spectrum shown in FIG. 16). In this graph, obvious differences between the solvated acetaminophen and precipitated acetaminophen spectra are seen. A comparison of FIGS. 13 and 14 reveals the similarities of the spectra of acetaminophen solvated by entirely different solvents and demonstrates the ability of Raman scattering to readily differentiate solvated from crystalline forms of a compound. Therefore, apparatus and methods of the disclosure may also be used to determine the difference between solvated acetaminophen and precipitated acetaminophen.

Figure 16:
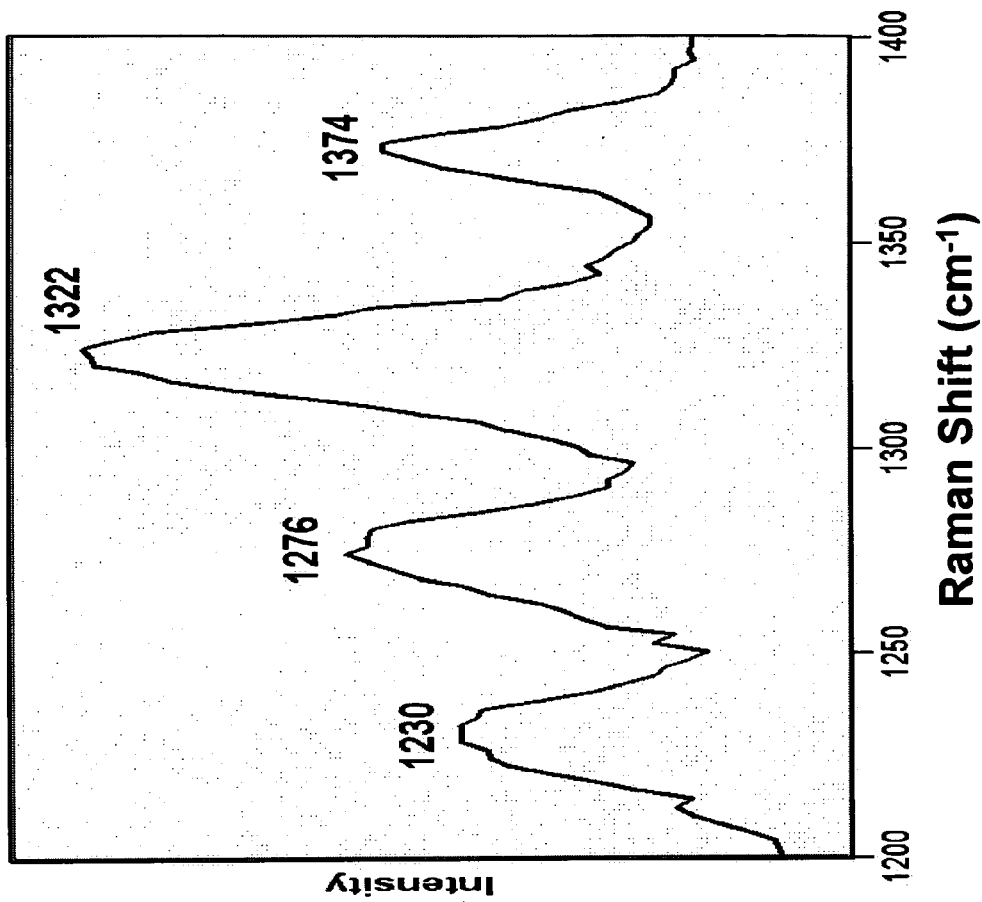
FIG. 16 is a spectrum of a solid solution of acetaminophen in polyvinypyrrolidone from which the image of FIG. 15 is taken.
Figure 15:
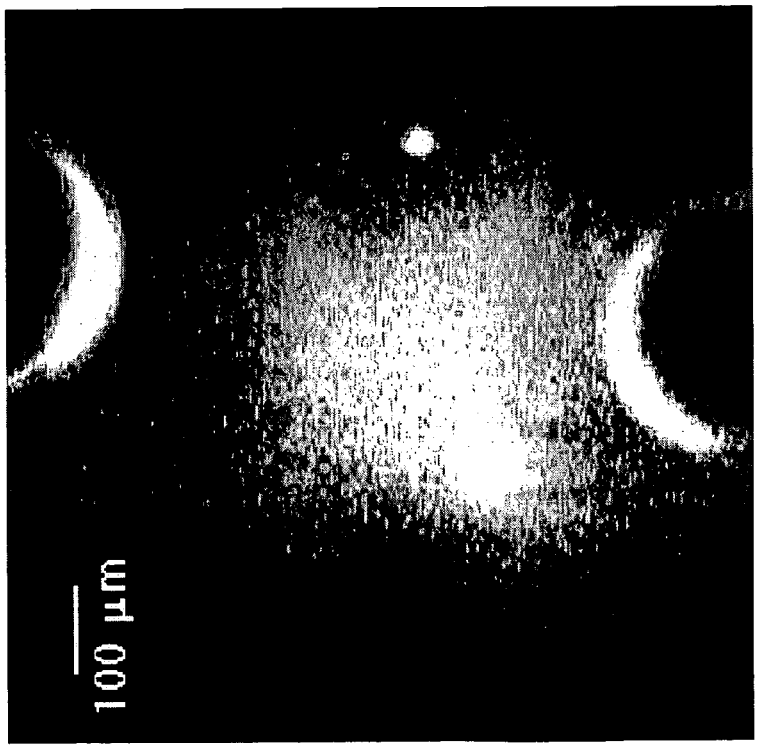
FIG. 15 is a Raman image at 1322 $cm^{-1}$ of a solid solution of acetaminophen in polyvinypyrrolidone.

FIGS. 14 through 18 relate to a solid solution of acetaminophen in polyvinypyrrolidone. The images and spectra were produced using apparatus and methods of embodiments of the disclosure. FIGS. 15 and 17 show Raman images of a solid solution of acetaminophen in polyvinypyrrolidone taken at 1322 cm$^{-1}$ and 1324 cm$^{-1}$, respectively. The bright area on the right side of the image in FIG. 17 shows the acetaminophen in solid form precipitated from the polyvinypyrrolidone. FIG. 16 is a spectrum of the solution of acetaminophen in polyvinypyrrolidone and shows a peak at 1322 cm$^{-1}$ where the image in FIG. 15 is taken.

FIG. 17 is a Raman image at 1324 cm$^{-1}$ of a solid solution of acetaminophen in polyvinypyrrolidone showing solvated acetaminophen (1702) and precipitated acetaminophen (1701) as indicated on the image. The differences in the appearance of the solvated and precipitated acetaminophen is striking in the image. FIG. 18 shows a spectrum of solvated acetaminophen (1802) superimposed with a spectrum of precipitated acetaminophen (1801) corresponding to areas 1702 and 1701 in FIG. 17, respectively. The differences between the spectra can be seen, for example, by comparing the relative positions of the peaks, representative of the Raman shift in cm$^{-1}$ and/or by the relative heights, representative of normalized intensity, of the peaks. Therefore, one of skill in the art can readily use FIGS. 17 18, either alone or in combination, to view the different states of acetaminophen as well as to determine a particular state of acetaminophen.

Figure 19:
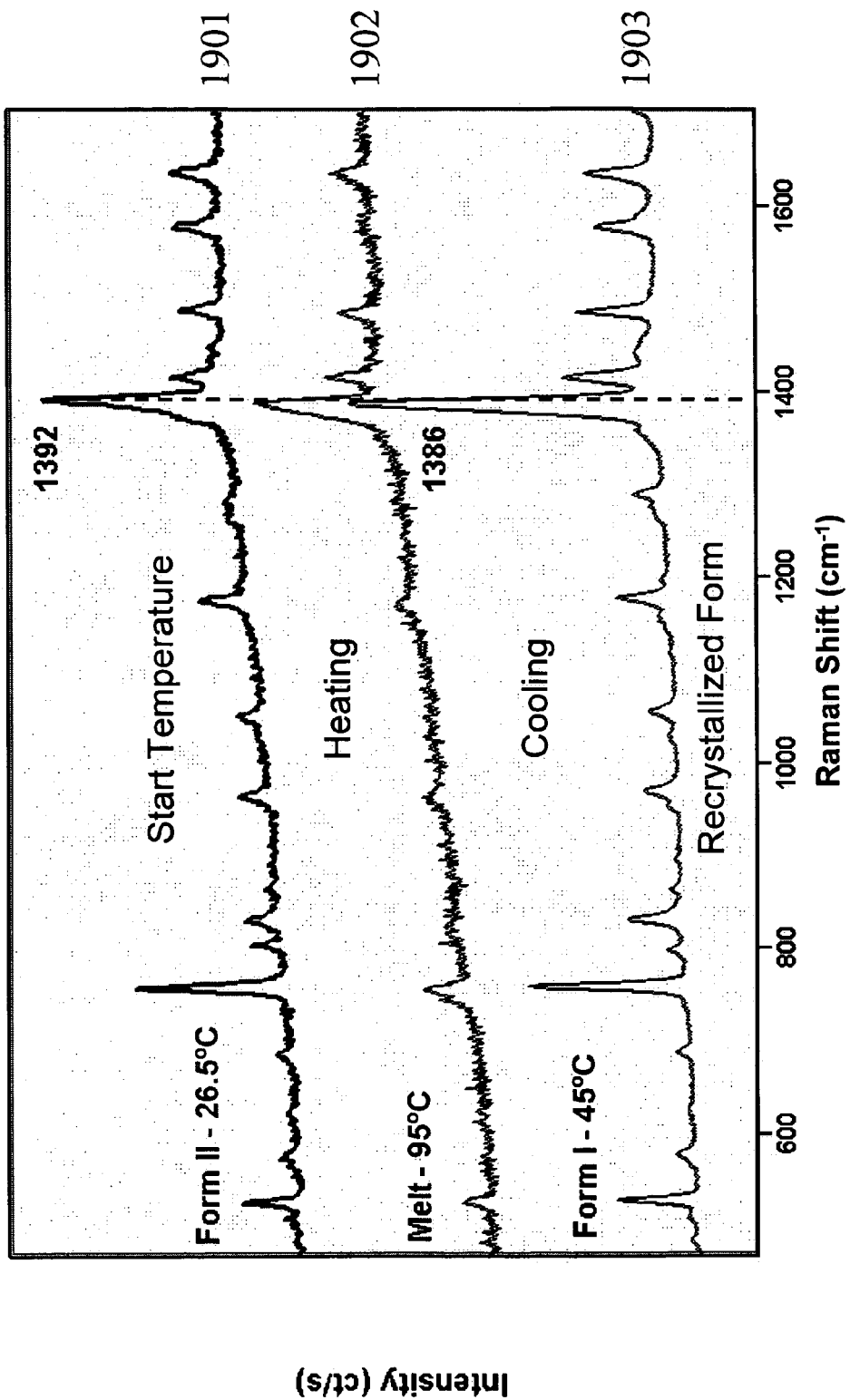
FIG. 19 is a graph showing the differences in the Raman spectra of nabumetone undergoing a thermal phase change.

FIG. 19 is a graph showing the differences in the Raman spectra of nabumetone undergoing a thermal phase change. The spectrum 1901 is the spectrum produced by nabumetone in a first solid state (i.e., Form I, the original crystallized form) at room temperature or, as shown, at a temperature of 45° C., still below the melting point. The spectrum 1902 is the spectrum produced by nabumetone in a liquefied state when heated to a temperature of 95° C. The spectrum 1903 is the spectrum produced by nabumetone in a second solid state (i.e., Form II, the recrystallized form) when subsequently cooled from the melt, while illuminating with the laser, to a temperature of 45° C. By comparing the spectra, for example by the relative peaks and the relative intensity levels of the peaks, the change of state of the nabumetone can be determined.

Figure 20:
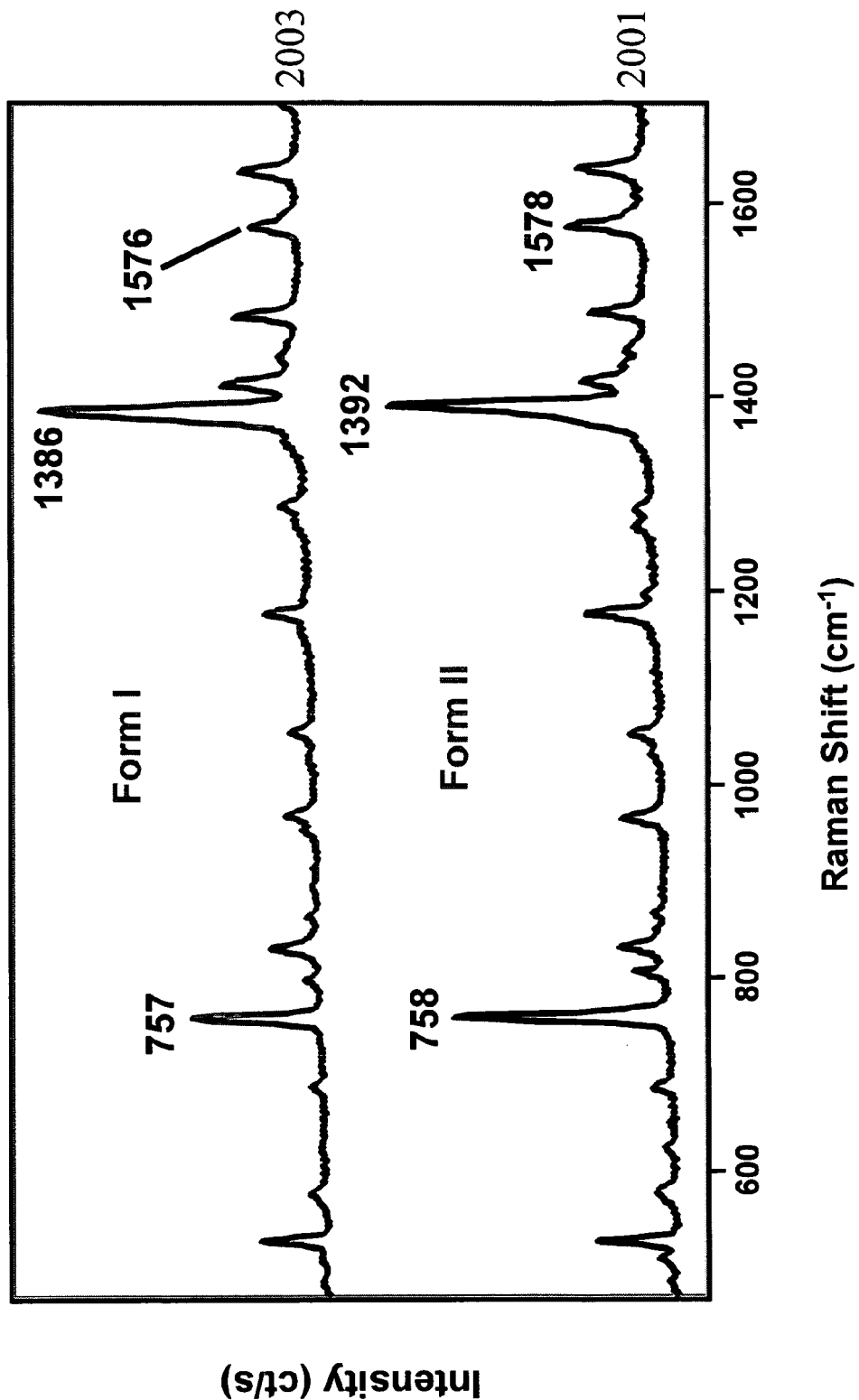
FIG. 20 is a graph detailing the differences in the Raman spectra between an original crystallized form of nabumetone and a recrystallized form of nabumetone from FIG. 19.

FIG. 20 is a graph detailing the differences in the Raman spectra between the Raman spectrum 2001 for a first solid state (i.e., Form II, the original crystallized form) of nabumetone and the Raman spectrum 2003 for a second solid state (i.e., Form I, the recrystallized form) of nabumetone from FIG. 19. As with the spectra in FIG. 19, comparing the spectra in FIG. 20 for, by example, the peak positions, peak shapes, and the relative intensity levels of the peaks, a difference between the two solid states of nabumetone can be determined. Therefore, it is possible to determine differences in the solid state, and in particular the crystalline form, of a material due to a temperature difference and/or a recent change of state.

FIG. 21 is a graph detailing the differences in the Raman spectra between the Raman spectrum 2103 for an original crystallized form (i.e., Form I) of nabumetone and the Raman spectrum 2101 for a recrystallized form (i.e., Form II) of nabumetone from FIG. 19. In FIG. 21, the two spectra are superimposed so that the differences between the spectra are more easily determined.

Given the ability to produce the images and spectra as described above, the apparatus and methods of the instant disclosure also allow for the production of streaming images and the comparison of spectra, as would be obvious to those of skill in the art consistent with the disclosed apparatus and methods. It would also be obvious to those of skill in the art that the above-described apparatus and methods can be used to produce images and spectra for more than just the few examples discussed above. Along with those mentioned above, the apparatus and methods of the disclosure would be useful, for example, in the understanding of polymorph formation with the ability to intervene and select a desired crystal structure; understanding the nature of protein aggregation and subsequent formation of amyloid fibers as well as provide insight into the ability to identify small molecules or biomolecules that interfere with this disease process; understanding the nature of semiconductor crystallization for purposes of, for example, growing materials of the desired stoichiometry and crystal structure; understanding the nature of covalent or ionic solid crystal formation to produce uniformity of structure in single crystals and for producing a desired polymorph which would be useful, for example, in applications related to photonic and microelectronic devices; characterizing and understanding the thermodynamic and kinetic forces at play in all forms of crystallization or aggregation in solution, polymer media or during a thermal phase transformation, etc. The aforementioned uses are exemplary only and should not be used to limit the disclosure in any way.

While preferred embodiments of the disclosed apparatus and method have been described, it is to be understood that the embodiments described are illustrative only and that the scope of the embodiments of the disclosed apparatus and method are to be defined solely by the appended claims when accorded a full range of equivalence, many variations and modifications naturally occurring to those of skill in the art from a perusal hereof.

I claim:

1. A method for producing a streaming spatially accurate wavelength-resolved image, comprising the steps of:
   (a) providing a sample for which an attribute of said sample changes as a function of time;
   (b) receiving and filtering scattered photons from said sample;
   (c) detecting a first group of said filtered photons with a photon detector at time $t_1$ to thereby obtain a first data stream representative of a first spatially accurate wavelength-resolved image;
   (d) detecting a second group of said filtered photons with a photon detector at time $t_2$ to thereby obtain a second data stream representative of a second spatially accurate wavelength-resolved image, wherein said time $t_2$ occurs a predetermined amount of time ("$\Delta t$") after time said $t_1$; and
   (e) sequentially displaying said first data stream and said second data stream to thereby produce a streaming spatially accurate wavelength-resolved image.

2. The method of claim 1 wherein said attribute is selected from the group consisting of: spatial displacement, chemical interaction, chemical state, physical state, phase, growth, shrinkage, diffusion, chemical decomposition, chemical metabolization, and physical strain.

3. The method of claim 1 wherein said attribute is selected from the group consisting of crystallization, dissolution, nucleation, and aggregation.

4. The method of claim 1 wherein said attribute is selected from the group consisting of defect density, purity, size, and morphology.

5. The method of claim 1 wherein said sample is a pharmaceutically active chemical selected from the group consisting of: acetaminophen; and nabumetone.

6. The method of claim 1 wherein said sample is a biological material selected from the group consisting of: protein, amyloid, and prion.

7. The method of claim 1 wherein said sample is a crystal material selected from the group consisting of: covalent crystal, ionic crystal, metallic crystal, and molecular crystal.

8. The method of claim 1 wherein said sample is a semiconductor material.

9. The method of claim 1 wherein $0 \text{ sec.} < \Delta t \leq 1 \text{ sec.}$ 10. The method of claim 1 wherein $1 \text{ sec.} \leq \Delta t \leq 30 \text{ sec.}$ 11. The method of claim 1 wherein $1 \text{ min.} \leq \Delta \leq 5 \text{ min.}$ 12. The method of claim 1 wherein $0 \text{ min.} < \Delta t \leq 10 \text{ min.}$ 13. The method of claim 1 wherein said step of receiving and filtering scattered photons from said sample includes using a filter selected from the group consisting of: liquid crystal tunable filter, acoustic optical filter, and imaging interferometer.

14. The method of claim 1 wherein said step of receiving and filtering scattered photons from said sample includes selectively collecting polarized scattered photons from said sample.

15. The method of claim 1 wherein said scattered photons from said sample are Raman scattered photons.

16. The method of claim 1 further comprising the step of (a1) illuminating said sample with illuminating photons to thereby produce said scattered photons from said sample.

17. The method of claim 16 wherein said illuminating photons are substantially monochromatic.

18. The method of claim 17 wherein said illuminating photons have a wavelength in the range of 200 nanometers to 1100 nanometers.

19. The method of claim 16 wherein said illuminating photons are polarized.

20. The method of claim 16 wherein said illuminating photons strike said sample at an angle that is oblique to a plane along which said sample is substantially oriented.

21. The method of claim 16 wherein said illuminating photons strike said sample on a side of said sample other than a side that is closest to said photon detector.

22. The method of claim 1 wherein said photon detector is selected from the group consisting of: charge coupled device ("CCD"), complementary metal oxide semiconductor ("CMOS") camera, avalanche photodiode array, and focal plane array.

23. The method of claim 1 wherein said step of displaying includes displaying said first data stream and said second data stream so that said streaming spatially accurate wavelength-resolved image appears in a visually-readable form.

24. The method of claim 1 further comprising the steps of:
   (f) storing said first data stream;
   (g) storing said second data stream; and
   (h) combining said first data stream and said second data stream.

25. The method of claim 1 wherein said photon detector comprises a first photon detector and a second photon detector, said first photon detector detecting said first group of filtered photons and said second photon detector detecting said second group of filtered photons.

26. A method for producing a streaming spatially accurate wavelength-resolved image, comprising the steps of:
   (a) providing a sample comprising a molecular crystal for which an attribute of said sample changes as a function of time, wherein said attribute is selected from the group consisting of: crystallization, dissolution, nucleation, and aggregation;
   (b) illuminating said sample with substantially monochromatic photons produced by a laser thereby producing Raman scattered photons from said sample, wherein the wavelength of said substantially monochromatic photons are in the range of 200 nanometers to 1100 nanometers;
(c) filtering said Raman scattered photons using a liquid crystal tunable filter;
(d) detecting a first group of said filtered photons with a charge coupled device at time $t_1$ to thereby obtain a first data stream representative of a first spatially accurate wavelength-resolved image;
(e) storing said first data stream;
(f) detecting a second group of said filtered photons with a charge coupled device at time $t_2$ to thereby obtain a second data stream representative of a second spatially accurate wavelength-resolved image, wherein time $t_2$ occurs less than 10 minutes after said time $t_1$; and
(g) sequentially displaying said first data stream and second data stream to thereby produce a streaming spatially accurate wavelength-resolved image that appears in a visually-readable form.

27. A method for producing a streaming spatially accurate wavelength-resolved image, comprising the steps of:
(a) providing a sample comprising a solvent and a solute for which an attribute of said sample changes as a function of time, wherein said attribute is selected from the group consisting of: crystallization, dissolution, nucleation, and aggregation;
(b) illuminating said sample with substantially monochromatic photons produced by a laser thereby producing Raman scattered photons from said sample, wherein the wavelength of said substantially monochromatic photons are in the range of 200 nanometers to 1100 nanometers;
(c) filtering said Raman scattered photons using a liquid crystal tunable filter;
(d) detecting a first group of said filtered photons with a charge coupled device at time $t_1$ to thereby obtain a first data stream representative of a first spatially accurate wavelength-resolved image;
(e) storing said first data stream;
(f) detecting a second group of said filtered photons with a charge coupled device at time $t_2$ to thereby obtain a second data stream representative of a second spatially accurate wavelength-resolved image, wherein time $t_2$ occurs less than 10 minutes after time $t_1$; and
(g) sequentially displaying said first data stream and second data stream to thereby produce a streaming spatially accurate wavelength-resolved image that appears in a visually-readable form.

28. A method for producing a streaming spatially accurate wavelength-resolved image, comprising the steps of:
(a) providing a sample comprising a liquid for which an attribute of said sample changes as a function of time, wherein the attribute is selected from the group consisting of: crystallization, dissolution, nucleation, and aggregation;
(b) illuminating said sample with substantially monochromatic photons produced by a laser thereby producing Raman scattered photons from said sample, wherein the wavelength of said substantially monochromatic photons are in the range of 200 nanometers to 1100 nanometers;
(c) filtering said Raman scattered photons using a liquid crystal tunable filter;
(d) detecting a first group of the filtered photons with a charge coupled device at time $t_1$ to thereby obtain a first data stream representative of a first spatially accurate wavelength-resolved image;
(e) storing said first data stream;
(f) detecting a second group of said filtered photons with a charge coupled device at time $t_2$ to thereby obtain a second data stream representative of a second spatially accurate wavelength-resolved image, wherein time $t_2$ occurs less than 10 minutes after time $t_1$; and
(g) sequentially displaying said first data stream and second data stream to thereby produce a streaming spatially accurate wavelength-resolved image that appears in a visually-readable form.

29. A method for producing a streaming spatially accurate wavelength-resolved image, comprising the steps of:
(a) providing a sample for which an attribute of said sample changes as a function of time;
(b) filtering photons emitted by said sample;
(c) detecting a first group of said filtered photons with a photon detector at time $t_1$ to thereby obtain a first data stream representative of a first spatially accurate wavelength-resolved image;
(d) detecting a second group of the filtered photons with a photon detector at time $t_2$ to thereby obtain a second data stream representative of a second spatially accurate wavelength-resolved image, wherein time $t_2$ occurs a predetermined amount of time ("$\Delta t$") after time $t_1$; and
(e) sequentially displaying said first data stream and said second data stream to thereby produce a streaming spatially accurate wavelength-resolved image.

30. The method of claim 29 wherein said attribute is selected from the group consisting of: spatial displacement, chemical interaction, chemical state, physical state, phase, growth, shrinkage, diffusion, chemical decomposition, chemical metabolization, and physical strain.

31. The method of claim 29 wherein said attribute is selected from the group consisting of crystallization, dissolution, nucleation, and aggregation.

32. The method of claim 29 wherein said attribute is selected from the group consisting of defect density, purity, size, and morphology.

33. The method of claim 29 wherein said sample is a pharmaceutically active chemical selected from the group consisting of: acetaminophen and nabutemone.

34. The method of claim 29 wherein said sample is a biological material selected from the group consisting of: protein, amyloid, and prion.

35. The method of claim 29 wherein said sample is a crystal material selected from the group consisting of: covalent crystal, ionic crystal, metallic crystal, and molecular crystal.

36. The method of claim 29 wherein said sample is a semiconductor material.

37. The method of claim 29 wherein $0 \text{ sec.} < \Delta t \leq 1 \text{ sec.}$ 38. The method of claim 29 wherein $1 \text{ sec.} \leq \Delta t \leq 30 \text{ sec.}$ 39. The method of claim 29 wherein $1 \text{ min.} \leq \Delta t \leq 5 \text{ min.}$ 40. The method of claim 29 wherein $0 \text{ min.} < \Delta t \leq 10 \text{ min.}$ 41. The method of claim 29 wherein said step of filtering photons emitted by said sample includes using a filter selected from the group consisting of: liquid crystal tunable filter, acoustic optical filter, and imaging interferometer.

42. The method of claim 29 wherein said step of filtering photons emitted by said sample includes selectively collecting polarized photons emitted by said sample.

43. The method of claim 29 wherein said photon detector is selected from the group consisting of: charge coupled device ("CCD"), complementary metal oxide semiconductor ("CMOS") camera, avalanche photodiode array, and focal plane array.

44. The method of claim 29 wherein said step of displaying includes displaying said first data stream and said second data stream so that the streaming spatially accurate wavelength-resolved image appears in a visually-readable form.

45. The method of claim 29 further comprising the steps of:
(f) storing said first data stream;
(g) storing said second data stream; and
(h) combining said first data stream and said second data stream.

46. The method of claim 29 wherein said photon detector comprises a first photon detector and a second photon detector, said first photon detector detecting said first group of filtered photons and said second photon detector detecting said second group of filtered photons.

47. A method for producing a streaming spatially accurate wavelength-resolved image, comprising the steps of:
(a) providing a sample comprising a molecular crystal for which an attribute of said sample changes as a function of time, wherein said attribute is selected from the group consisting of: crystallization, dissolution, nucleation, and aggregation;
(b) filtering photons emitted by said sample using a liquid crystal tunable filter;
(c) detecting a first group of said filtered photons with a charge coupled device at time $t_1$ to thereby obtain a first data stream representative of a first spatially accurate wavelength-resolved image;
(d) storing said first data stream;
(e) detecting a second group of said filtered photons with a charge coupled device at time $t_2$ to thereby obtain a second data stream representative of a second spatially accurate wavelength-resolved image, wherein time $t_2$ occurs less than 10 minutes after time $t_1$; and
(f) sequentially displaying said first data stream and said second data stream to thereby produce a streaming spatially accurate wavelength-resolved image that appears in a visually-readable form.

48. A method for producing a streaming spatially accurate wavelength-resolved image, comprising the steps of:
(a) providing a sample comprising a solvent and a solute for which an attribute of said sample changes as a function of time, wherein said attribute is selected from the group consisting of: crystallization, dissolution, nucleation, and aggregation;
(b) filtering photons emitted by said sample using a liquid crystal tunable filter;
(c) detecting a first group of said filtered photons with a charge coupled device at time $t_1$ to thereby obtain a first data stream representative of a first spatially accurate wavelength-resolved image;
(d) storing said first data stream;
(e) detecting a second group of said filtered photons with a charge coupled device at time $t_2$ to thereby obtain a second data stream representative of a second spatially accurate wavelength-resolved image, wherein time $t_2$ occurs less than 10 minutes after time $t_1$; and
(f) sequentially displaying said first data stream and said second data stream to thereby produce a streaming spatially accurate wavelength-resolved image that appears in a visually-readable form.

49. A method for producing a streaming spatially accurate wavelength-resolved image, comprising the steps of:
(a) providing a sample comprising a liquid for which an attribute of said sample changes as a function of time, wherein said attribute is selected from the group consisting of: crystallization, dissolution, nucleation, and aggregation;
(b) filtering photons emitted by said sample using a liquid crystal tunable filter;
(c) detecting a first group of said filtered photons with a charge coupled device at time $t_1$ to thereby obtain a first data stream representative of a first spatially accurate wavelength-resolved image;
(d) storing said first data stream;
(e) detecting a second group of said filtered photons with a charge coupled device at time $t_2$ to thereby obtain a second data stream representative of a second spatially accurate wavelength-resolved image, wherein time $t_2$ occurs less than 10 minutes after time $t_1$; and
(f) sequentially displaying said first data stream and said second data stream to thereby produce a streaming spatially accurate wavelength-resolved image that appears in a visually-readable form.

50. An apparatus for producing a streaming spatially accurate wavelength-resolved image, comprising:
a sample for which an attribute of said sample changes as a function of time;
a filter for filtering scattered photons from said sample;
at least one photon detector for detecting a first group of said filtered photons at time $t_1$ to thereby obtain a first data stream representative of a first spatially accurate wavelength-resolved image, and for detecting a second group of said filtered photons at time $t_2$ to thereby obtain a second data stream representative of a second spatially accurate wavelength-resolved image, wherein time $t_2$ occurs a predetermined amount of time ("$\Delta t$") after time $t_1$; and
display means for sequentially displaying said first data stream and said second data stream to thereby produce a streaming spatially accurate wavelength-resolved image.

51. The apparatus of claim 50 wherein said attribute is selected from the group consisting of: spatial displacement, chemical interaction, chemical state, physical state, phase, growth, shrinkage, diffusion, chemical decomposition, chemical metabolization, and physical strain.

52. The apparatus of claim 50 wherein said attribute is selected from the group consisting of crystallization, dissolution, nucleation, and aggregation.

53. The apparatus of claim 50 wherein said attribute is selected from the group consisting of defect density, purity, size, and morphology.

54. The apparatus of claim 50 wherein said sample is a pharmaceutically active chemical selected from the group consisting of: acetaminophen and nabumetone.

55. The apparatus of claim 50 wherein said sample is a biological material selected from the group consisting of: protein, amyloid, and prion.

56. The apparatus of claim 50 wherein the sample is a crystal material selected from the group consisting of: covalent crystal, ionic crystal, metallic crystal, and molecular crystal.

57. The apparatus of claim 50 wherein said sample is a semiconductor material.

58. The apparatus of claim 50 wherein $0 \text{ sec.} < \Delta t \leq 1 \text{ sec.}$ 59. The apparatus of claim 50 wherein $1 \text{ sec.} \leq \Delta t \leq 30 \text{ sec.}$ 60. The apparatus of claim 50 wherein $1 \text{ min.} \leq \Delta t \leq 5 \text{ min.}$ 61. The apparatus of claim 50 wherein $0 \text{ min.} < \Delta t \leq 10 \text{ min.}$ 62. The apparatus of claim 50 wherein said filter is selected from the group consisting of: liquid crystal tunable filter, acoustic optical filter, and imaging interferometer.

63. The apparatus of claim 50 wherein said filter selectively collects polarized scattered photons from said sample.

64. The apparatus of claim 50 wherein said scattered photons from said sample are Raman scattered photons.

65. The apparatus of claim 50 further comprising: a photon source for illuminating said sample with illuminating photons to thereby produce said scattered photons from said sample.

66. The apparatus of claim 65 wherein the illuminating photons are substantially monochromatic.

67. The apparatus of claim 66 wherein said illuminating photons have a wavelength in the range of 200 nanometers to 1100 nanometers.

68. The apparatus of claim 65 wherein said illuminating photons are polarized.

69. The apparatus of claim 65 wherein said illuminating photons strike said sample at an angle that is oblique to a plane along which said sample is substantially oriented.

70. The apparatus of claim 65 wherein said illuminating photons strike said sample on a side of said sample other than a side that is closest to said at least one photon detector.

71. The apparatus of claim 50 wherein said photon detector is selected from the group consisting of: charge coupled device ("CCD"), complementary metal oxide semiconductor ("CMOS") camera, avalanche photodiode array, and focal plane array.

72. The apparatus of claim 50 wherein said display means displays said first data stream and said second data stream so that the streaming spatially accurate wavelength-resolved image appears in a visually-readable form.

73. The apparatus of claim 50 further comprising:
means for storing said first data stream and said second data stream; and
combining means for combining said first data stream and said second data stream.

74. The apparatus of claim 50 wherein a first photon detector detects said first group of filtered photons and a second photon detector detects said second group of filtered photons.

75. An apparatus for producing a streaming spatially accurate wavelength-resolved image, comprising:
a sample comprising a molecular crystal for which an attribute of said sample changes as a function of time, wherein said attribute is selected from the group consisting of: crystallization, dissolution, nucleation, and aggregation;
a laser for illuminating said sample with substantially monochromatic photons thereby producing Raman scattered photons from said sample, wherein the wavelength of said substantially monochromatic photons are in the range of 200 nanometers to 1100 nanometers;
a liquid crystal tunable filter for filtering said Raman scattered photons;
a charge coupled device for detecting a first group of said filtered photons at time $t_1$ to thereby obtain a first data stream representative of a first spatially accurate wavelength-resolved image and for detecting a second group of said filtered photons at time $t_2$ to thereby obtain a second data stream representative of a second spatially accurate wavelength-resolved image, wherein time $t_2$ occurs less that 10 minutes after time $t_1$;
storage means for storing said first data stream; and
display means for sequentially displaying said first data stream and said second data stream to thereby produce a streaming spatially accurate wavelength-resolved image that appears in a visually-readable form.

76. An apparatus for producing a streaming spatially accurate wavelength-resolved image, comprising:
a sample comprising a solvent and a solute for which an attribute of said sample changes as a function of time, wherein said attribute is selected from the group consisting of: crystallization, dissolution, nucleation, and aggregation;
a laser for illuminating said sample with substantially monochromatic photons thereby producing Raman scattered photons from said sample, wherein the wavelength of said substantially monochromatic photons are in the range of 200 nanometers to 1100 nanometers;
a liquid crystal tunable filter for filtering said Raman scattered photons;
a charge coupled device for detecting a first group of said filtered photons at time $t_1$ to thereby obtain a first data stream representative of a first spatially accurate wavelength-resolved image and for detecting a second group of said filtered photons at time $t_2$ to thereby obtain a second data stream representative of a second spatially accurate wavelength-resolved image, wherein time $t_2$ occurs less that 10 minutes after time $t_1$;
storage means for storing said first data stream; and
display means for sequentially displaying said first data stream and said second data stream to thereby produce a streaming spatially accurate wavelength-resolved image that appears m a visually-readable form.

77. An apparatus for producing a streaming spatially accurate wavelength-resolved image, comprising:
a sample comprising a liquid for which an attribute of said sample changes as a function of time, wherein said attribute is selected from the group consisting of: crystallization, dissolution, nucleation, and aggregation;
a laser for illuminating said sample with substantially monochromatic photons thereby producing Raman scattered photons from said sample, wherein the wavelength of said substantially monochromatic photons are in the range of 200 nanometers to 1100 nanometers;
a liquid crystal tunable filter for filtering said Raman scattered photons;
a charge coupled device for detecting a first group of said filtered photons at time $t_1$ to thereby obtain a first data stream representative of a first spatially accurate wavelength-resolved image and for detecting a second group of said filtered photons at time $t_2$ to thereby obtain a second data stream representative of a second spatially accurate wavelength-resolved image, wherein time occurs less that 10 minutes after time $t_1$; storage means for storing said first data stream; and
display means for sequentially displaying said first data stream and said second data stream to thereby produce a streaming spatially accurate wavelength-resolved image that appears in a visually-readable form.

78. An apparatus for producing a streaming spatially accurate wavelength-resolved image, comprising:
a sample for which an attribute of said sample changes as a function of time;
a filter for filtering photons emitted by said sample;
a photon detector for detecting a first group of said filtered photons at time $t_1$ to thereby obtain a first data stream representative of a first spatially accurate wavelength-resolved image and for detecting a second group of said filtered photons at time $t_2$ to thereby obtain a second data stream representative of a second spatially accurate wavelength-resolved image, wherein time $t_2$ occurs a predetermined amount of time ("$\Delta t$") after time $t_1$; and
display means for sequentially displaying said first data stream and said second data stream to thereby produce a streaming spatially accurate wavelength-resolved image.

79. The apparatus of claim 78 wherein said attribute is selected from the group consisting of: spatial displacement, chemical interaction, chemical state, physical state, phase, growth, shrinkage, diffusion, chemical decomposition, chemical metabolization, and physical strain.

80. The apparatus of claim 78 wherein said attribute is selected from the group consisting of: crystallization, dissolution, nucleation, and aggregation.

81. The apparatus of claim 78 wherein said attribute is selected from the group consisting of defect density, purity, size, and morphology.

82. The apparatus of claim 78 wherein said sample is a pharmaceutically active chemical selected from the group consisting of: acetaminophen and nabumetone.

83. The apparatus of claim 78 wherein said sample is a biological material selected from the group consisting of: protein, amyloid, and prion.

84. The apparatus of claim 78 wherein said sample is a crystal material selected from the group consisting of: covalent crystal, ionic crystal, metallic crystal, and molecular crystal.

85. The apparatus of claim 78 wherein said sample is a semiconductor material.

86. The apparatus of claim 78 wherein 0 sec.$<\Delta t \leq 1$ sec.

87. The apparatus of claim 78 wherein 1 sec.$\leq \Delta t \leq 30$ sec.

88. The apparatus of claim 78 wherein 1 min.$\leq \Delta t \leq 5$ min.

89. The apparatus of claim 78 wherein 0 min.$<\Delta t \leq 10$ min.

90. The apparatus of claim 78 wherein said step of filtering photons emitted by said sample includes using a filter selected from the group consisting of: liquid crystal tunable filter, acoustic optical filter, and imaging interferometer.

91. The apparatus of claim 78 wherein said step of filtering photons emitted by said sample includes selectively collecting polarized photons emitted by said sample.

92. The apparatus of claim 78 wherein said photon detector is selected from the group consisting of: charge coupled device ("CCD"), complementary metal oxide semiconductor ("CMOS") camera, avalanche photodiode array, and focal plane array.

93. The apparatus of claim 78 wherein said step of displaying includes displaying said first data stream and said second data stream so that the streaming spatially accurate wavelength-resolved image appears in a visually-readable form.

94. The apparatus of claim 78 further comprising:
means for storing said first data stream and said second data stream; and
combining means for combining said first data stream and said second data stream.

95. The apparatus of claim 78 wherein said photon detector comprises a first photon detector and a second photon detector, said first photon detector detecting said first group of filtered photons and said second photon detector detecting said second group of filtered photons.

96. An apparatus for producing a streaming spatially accurate wavelength-resolved image, comprising:
a sample comprising a molecular crystal for which an attribute of said sample changes as a function of time, wherein said attribute is selected from the group consisting of: crystallization, dissolution, nucleation, and aggregation;
a liquid crystal tunable filter for filtering photons emitted by said sample;
a charge coupled device for detecting a first group of said filtered photons at time $t_1$ to thereby obtain a first data stream representative of a first spatially accurate wavelength-resolved image and for detecting a second group of said filtered photons at time $t_2$ to thereby obtain a second data stream representative of a second spatially accurate wavelength-resolved image, wherein time $t_2$ occurs less that 10 minutes after time $t_1$;
storage means for storing said first data stream; and
display means for sequentially displaying said first data stream and said second data stream to thereby produce a streaming spatially accurate wavelength-resolved image that appears in a visually-readable form.

97. An apparatus for producing a streaming spatially accurate wavelength-resolved image, comprising:
a sample comprising a solvent and a solute for which an attribute of said sample changes as a function of time, wherein said attribute is selected from the group consisting of:
crystallization, dissolution, nucleation, and aggregation;
a liquid crystal tunable filter for filtering photons emitted by said sample;
a charge coupled device for detecting a first group of said filtered photons at time $t_1$ to thereby obtain a first data stream representative of a first spatially accurate wavelength-resolved image and for detecting a second group of said filtered photons at time $t_2$ to thereby obtain a second data stream representative of a second spatially accurate wavelength-resolved image, wherein time $t_2$ occurs less that 10 minutes after time $t_1$;
storage means for storing said first data stream; and
display means for sequentially displaying said first data stream and said second data stream to thereby produce a streaming spatially accurate wavelength-resolved image that appears in a visually-readable form.

98. An apparatus for producing a streaming spatially accurate wavelength-resolved image, comprising:
a sample comprising a liquid for which an attribute of said sample changes as a function of time, wherein said attribute is selected from the group consisting of: crystallization, dissolution, nucleation, and aggregation;
a liquid crystal tunable filter for filtering photons emitted by said sample;
a charge coupled device for detecting a first group of said filtered photons at time $t_1$ to thereby obtain a first data stream representative of a first spatially accurate wavelength-resolved image and for detecting a second group of said filtered photons at time $t_2$ to thereby obtain a second data stream representative of a second spatially accurate wavelength-resolved image, wherein time $t_2$ occurs less that 10 minutes after time $t_1$;
storage means for storing said first data stream; and
display means for sequentially displaying said first data stream and said second data stream to thereby produce a streaming spatially accurate wavelength-resolved image that appears in a visually-readable form.

99. The method of claim 16 wherein said illuminating photons are produced by a device selected from the group consisting of: laser, light emitting diode, and white light source, wherein said device is used in conjunction with a grating or wavelength tunable filter.

100. The apparatus of claim 65 wherein said illuminating photons are produced by a photon source selected from the group consisting of: laser, light emitting diode, and white light source, wherein said photon source is used in conjunction with a grating or wavelength tunable filter.

* * * * *